(12) United States Patent
Sugimoto et al.

(10) Patent No.: US 10,092,556 B2
(45) Date of Patent: Oct. 9, 2018

(54) PIPERIDINE COMPOUND OR SALT THEREOF

(71) Applicant: TAIHO PHARMACEUTICAL CO., LTD., Chiyoda-ku (JP)

(72) Inventors: Tetsuya Sugimoto, Tsukuba (JP); Hidekazu Takahashi, Tsukuba (JP); Morihiro Mitsuya, Tsukuba (JP); Norio Masuko, Tsukuba (JP); Hiroshi Sootome, Tsukuba (JP)

(73) Assignee: TAIHO PHARMACEUTICAL CO., LTD., Chiyoda-ku (JP)

( * ) Notice: Subject to any disclaimer, the term of this patent is extended or adjusted under 35 U.S.C. 154(b) by 0 days.

(21) Appl. No.: 15/131,372

(22) Filed: Apr. 18, 2016

(65) Prior Publication Data

US 2016/0228427 A1    Aug. 11, 2016

Related U.S. Application Data

(62) Division of application No. 14/381,814, filed as application No. PCT/JP2013/055064 on Feb. 27, 2013, now Pat. No. 9,346,787.

(30) Foreign Application Priority Data

Feb. 29, 2012 (JP) ................................. 2012-043303
Aug. 27, 2012 (JP) ................................. 2012-186534

(51) Int. Cl.
A61K 31/4545 (2006.01)
C07D 401/14 (2006.01)
(Continued)

(52) U.S. Cl.
CPC ........ *A61K 31/4545* (2013.01); *A61K 31/337* (2013.01); *A61K 45/06* (2013.01);
(Continued)

(58) Field of Classification Search
CPC .............. A61K 31/4545; A61K 31/337; C07D 401/14; C07D 413/14; C07D 417/14
(Continued)

(56) References Cited

U.S. PATENT DOCUMENTS 8,519,136 B2 * 8/2013 Kato ................... C07D 401/14
546/194
2007/0142368 A1 6/2007 Xiao et al.
(Continued)

FOREIGN PATENT DOCUMENTS

CN 101528731 A 9/2009
JP 2008-081492 A 4/2008
(Continued)

OTHER PUBLICATIONS

Swami et al. "Eribulin in . . . " Marine drugs v. 13, pp. 5016-5058 (2015).*
Fluorinated Pharmaceutical, Wakefeild 2003 http://web.archive.org/web/20030905122408/http://www.iptonline.com/articles/public/IPTFOUR74NP.pdf. (accessed via Wayback machine Nov. 20, 2009 showing web availability as of Sep. 2003).*
Wermuth, Molecular Variations Based on Isosteric Replacements 1996.*
Silvia Lapenna, et al., "Cell cycle kinases as therapeutic targets for cancer" Nature Reviews, Drug Discovery, vol. 8, Jul. 2009, pp. 547-566.
Giannis Mountzios, et al., "Aurora kinases as targets for cancer therapy" Cancer Treatment Reviews, vol. 34, 2008, pp. 175-182.
Hiroshi Y. Yamada, et al., "Spindle checkpoint function and cellular sensitivity to antimitotic drugs" Molecular Cancer Therapeutics, vol. 5, No. 12, Dec. 2006, pp. 2963-2969.
(Continued)

*Primary Examiner* — Rita J Desai
(74) *Attorney, Agent, or Firm* — Oblon, McClelland, Maier & Neustadt, L.L.P.

(57) ABSTRACT

A novel compound which has an excellent aurora A-selective inhibitory action and is useful as an orally administrable anticancer agent is provided. Also, a novel agent for potentiation of anti-tumor effect of microtubule agonists, which include a taxane anticancer agent, and a combination therapy are provided. A piperidine compound represented by a general formula (I) or a salt thereof:

wherein, $R_1$ represents a carboxyl group, $-C(=O)NR_5R_6$, or an oxadiazolyl group optionally having a $C_1$-$C_6$ alkyl group or a trifluoromethyl group as a substituent;

$R_2$ represents a halogen atom or a $C_1$-$C_6$ alkoxy group;

$R_3$ represents a phenyl group optionally having 1 to 3 same or different group(s) selected from a halogen atom, a $C_1$-$C_6$ alkyl group, a $C_1$-$C_6$ alkoxy group, and a trifluoromethyl group as a substituent;

$R_4$ represents a hydrogen atom or a $C_1$-$C_6$ alkyl group; and $R_5$ and $R_6$ are the same or different and each represent a hydrogen atom, a $C_1$-$C_6$ alkyl group, or a $C_3$-$C_6$ cycloalkyl group, or $R_5$ and $R_6$ optionally form a 3 to 6-membered nitrogen-containing saturated heterocyclic group together with a nitrogen atom to which $R_5$ and $R_6$ are bound, are provided.

(I)

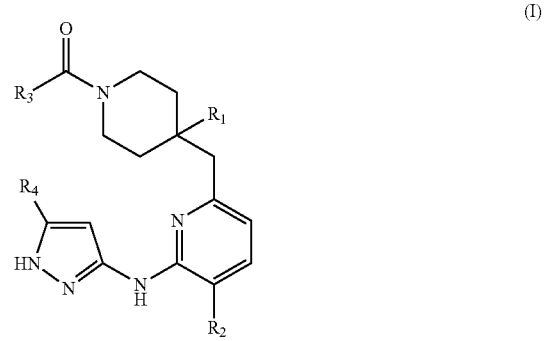

21 Claims, No Drawings

(51) Int. Cl.
*C07D 413/14* (2006.01)
*A61K 31/337* (2006.01)
*C07D 417/14* (2006.01)
*A61K 45/06* (2006.01)

(52) U.S. Cl.
CPC ......... *C07D 401/14* (2013.01); *C07D 413/14* (2013.01); *C07D 417/14* (2013.01)

(58) Field of Classification Search
USPC ........................................................ 514/318
See application file for complete search history.

(56) References Cited

U.S. PATENT DOCUMENTS

| | | |
|---|---|---|
| 2007/0173516 A1 | 7/2007 | Mortimore et al. |
| 2007/0219195 A1 | 9/2007 | Goldstein et al. |
| 2008/0058347 A1 | 3/2008 | Iwasawa et al. |
| 2008/0242667 A1 | 10/2008 | Adams et al. |
| 2009/0131461 A1 | 5/2009 | Davidson et al. |
| 2009/0264422 A1 | 10/2009 | Xiao et al. |
| 2010/0016335 A1 | 1/2010 | Iwasawa et al. |
| 2010/0222367 A1 | 9/2010 | Mortimore et al. |
| 2011/0003833 A1 | 1/2011 | Kato et al. |
| 2012/0029004 A1 | 2/2012 | Binch et al. |

FOREIGN PATENT DOCUMENTS

| | | |
|---|---|---|
| JP | 2008-540390 A | 11/2008 |
| JP | 2009-504771 A | 2/2009 |
| JP | 2009-506040 A | 2/2009 |
| JP | 2009-510107 A | 3/2009 |
| JP | 2009-530330 A | 8/2009 |
| JP | 2011-514309 A | 5/2011 |
| WO | 2008/026769 A1 | 3/2008 |
| WO | WO 2008/117175 A2 | 10/2008 |
| WO | WO 2008/117175 A3 | 10/2008 |
| WO | 2009/104802 A1 | 8/2009 |
| WO | WO2009104802 * | 8/2009 |
| WO | 2010/111050 A1 | 9/2010 |
| WO | 2010/111056 A1 | 9/2010 |

OTHER PUBLICATIONS

Shubha Anand, et al., "AURORA-A amplification overrides the mitotic spindle assembly checkpoint, inducing resistance to Taxol" Cancer Cell, vol. 3, Jan. 2003, pp. 51-62.
Tatsuo Hata, et al., "RNA Interference Targeting Aurora Kinase A Suppresses Tumor Growth and Enhances the Taxane Chemosensitivity in Human Pancreatic Cancer Cells" Cancer Research, vol. 65, No. 7, Apr. 1, 2005, pp. 2899-2905.
Phillip Kaestner, et al., "Determinants for the efficiency of anticancer drugs targeting either Aurora-A or Aurora-B kinases in human colon carcinoma cells" Molecular Cancer Therapeutics 2009, vol. 8, No. 7, Jul. 2009, pp. 2046-2056.
Klaus Dieterich, et al., "Homozygous mutation of AURKC yields large-headed polyploid spermatozoa and causes male infertility" Nature Genetics, vol. 39, No. 5, May 2007, pp. 661-665.
Xiaomei Yan, et al., "Aurora C is directly associated with Survivin and required for cytokinesis" Genes to Cells, vol. 10, 2005, pp. 617-626.
James D. Orth, et al., "Analysis of Mitosis and Antimitotic Drug Responses in Tumors by In Vivo Microscopy and Single-Cell Pharmacodynamics" Cancer Research, vol. 71, No. 13, Jul. 1, 2011, pp. 4608-4616.
George A. Patani et al., "Bioisosterism: A Rational Approach in Drug Design", Chemical Reviews vol. 96, No. 8, 1996, pp. 3147-3176.
Ahmed Kamal et al., "Remarkable enhancement in the DNA-binding ability of C2-fluoro substituted pyrrolo[2,1-c][1,4]benzodiazepines and their anticancer potential", Bioorganic & Medicinal Chemistry, vol. 17, 2009, pp. 1557-1572.
Indian Examination Report dated Mar. 28, 2018, in Application No. 7283/DELNP/2014, filed Aug. 29, 2014, 6 pages.
International Search Report dated Mar. 26, 2013 in PCT/JP2013/055064 filed Feb. 27, 2013.

* cited by examiner

PIPERIDINE COMPOUND OR SALT THEREOF

CROSS-REFERENCE TO RELATED APPLICATIONS

The present application is a divisional of U.S. application Ser. No. 14/381,814, filed Aug. 28, 2014, the entire contents of which are incorporated herein by reference. U.S. application Ser. No. 14/381,814 is a 371 of International Application No. PCT/JP2013/055064, filed Feb. 27, 2013 which is based upon and claims the benefits of priority to Japanese Application No. 2012-043303, filed Feb. 29, 2012 and Japanese Application No. 2012-186534, filed Aug. 27, 2012.

FIELD OF THE INVENTION

The present invention relates to a novel piperidine compound having the aurora A kinase inhibitory action or a salt thereof, and the use of the compound or a salt thereof.

BACKGROUND OF THE INVENTION

Aurora A is a member of serine-threonine kinases, and is widely involved in, for example, the formation and maturation of centrosomes, spindle dynamics, and chromosome alignment in the mitotic phase (M phase) of the cell cycle, thereby regulating the progression of mitosis (Non Patent Document 1). So far, overexpression and/or amplification of aurora A have been confirmed in a wide variety of carcinomas (Non Patent Document 2). Also, since inhibition of aurora A kinase in tumor cells induces not only termination of mitosis, but also apoptosis, aurora A is one of the important target molecules in cancer therapy.

Meanwhile, microtubule-targeting agents as represented by taxane and vinca alkaloid are widely used as the key drug in cancer chemotherapy. However, persistent and adequate therapeutic effects are not always obtained due to loss of responsiveness to drugs or becoming resistance to drugs. Therefore, there is clinical need for development of a drug capable of potentiating the anti-tumor effect of taxane drugs since such a drug promises to provide more effective therapeutic opportunities. The cytocidal effect of taxane anticancer agents requires activation of the spindle assembly checkpoint in the cell cycle, and there is a report that tumor cells having a reduced spindle assembly checkpoint activity show reduced sensitivity to taxane anticancer agents (Non Patent Document 3). In addition, it is known that a cell line overexpressing aurora A becomes resistance to paclitaxel (Non Patent Document 4) and inhibition of aurora A potentiates the activity of paclitaxel or docetaxel (Non Patent Document 5). Meanwhile, it has been reported that although aurora B, which is a subtype thereof, shows activity on the mitotic phase (M phase) of the cell cycle with aurora A, inhibition of aurora B reduces the spindle assembly checkpoint activity (Non Patent Document 6). Therefore, it is suggested that the inhibition of aurora B might attenuate the effect of taxane drugs. Also, aurora C is strongly expressed in, for example, testis or germ cells, and the results of human genome analysis have shown that aurora C is important in Spermatogenesis (Non Patent Document 7). The aurora C is known to function as complementation to the function of aurora B in cell division (Non Patent Document 8). Similarly to inhibition of aurora B, inhibition of aurora c induces aneuploidy in cells, leading to exhibiting phenotype which greatly differs from that exhibited by inhibition of aurora A, and potentiation of the effect of taxane drugs cannot presumably be expected. Furthermore, influence on the reproductive system cannot be overlooked, and therefore, it is desirable that the drug does not exhibit the inhibitory activity on aurora C.

According to above, it is expected that by administering a drug which selectively inhibits aurora A kinase in combination with a taxane anticancer agent, the drug will effectively potentiate the anti-tumor activity of the taxane anticancer agent, thereby enabling higher therapeutic effects.

Also, there is a report that the cell cycle termination activity induced by paclitaxel is sustained for several days in a mouse tumor model into which a human cancer cell line is transplanted (Non Patent Document 9). Therefore, an agent for oral administration is considered to be desirable when an aurora A inhibitor is to concomitantly administered, because of enabling continuous exposure.

So far, it has been reported that an aminopyridine derivative exhibiting the inhibitory activity on aurora A can be orally administered (Patent Document 1). However, although Patent Document 1 describes the inhibitory activity on aurora A and on cell proliferation in vitro, any descriptions relating to the evaluation of oral administration of the above compound are not found.

CITATION LIST

Patent Document

[Patent Document 1] WO2009/104802

Non Patent Document

[Non Patent Document 1] Nat. Rev. Drug Discov., 8, pp. 547 to 566 (2009)
[Non Patent Document 2] Cancer Treat. Rev., 34, pp. 175 to 182 (2008)
[Non Patent Document 3] Mol. Cancer Ther., 5, pp. 2963 to 2969 (2006)
[Non Patent Document 4] Cancer Cell, 3, pp. 51 to 62 (2003)
[Non Patent Document 5] Cancer Res., 65, pp. 2899 to 2905 (2005)
[Non Patent Document 6] Mol. Cancer Ther., 8, pp. 2046 to 2056 (2009)
[Non Patent Document 7] Nature Genet. 39: pp. 661 to 665, 2007
[Non Patent Document 8] Genes Cells 10: pp. 617 to 626, 2005
[Non Patent Document 9] Cancer Res., 71, pp. 4608 to 4616 (2011)

SUMMARY OF THE INVENTION

Problem to be Solved by the Invention

Accordingly, an object of the present invention is to provide a novel compound which shows an excellent aurora A-selective inhibitory activity and is useful as an orally administrable anticancer agent. Further, another object of the present is to provide a novel agent for potentiation of anti-tumor effect of microtubule-targeting agents containing a taxane anticancer agent, and a combination therapy.

Means for Solving the Problem

The present inventors conducted intensive research in order to solve the aforementioned objects. As a result, they found that piperidine compound having a specific substituent on the pyridine ring shows an excellent aurora A-selective inhibitory activity and cancer cell proliferation inhibitory action, and is orally administrable. They further found that such a piperidine compound remarkably potentiated the anti-tumor effects of microtubule-targeting agents containing a taxane anticancer agent, thereby completing the present invention.

Specifically, the present invention provides a piperidine compound represented by a general formula (I) or a salt thereof:

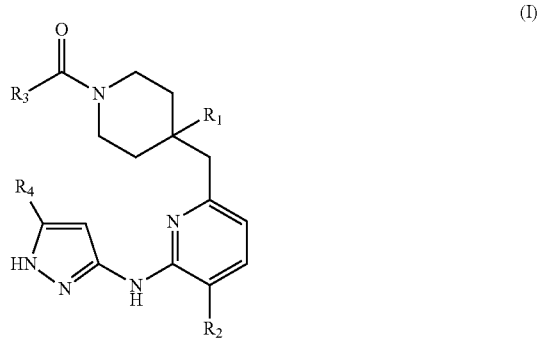

(I)

wherein, $R_1$ represents a carboxyl group, $-C(=O)NR_5R_6$, or an oxadiazolyl group optionally having a $C_1$-$C_6$ alkyl group or a trifluoromethyl group as a substituent;

$R_2$ represents a halogen atom or a $C_1$-$C_6$ alkoxy group;

$R_3$ represents a phenyl group optionally having 1 to 3 same or different group(s) selected from a halogen atom, a $C_1$-$C_6$ alkyl group, a $C_1$-$C_6$ alkoxy group, and a trifluoromethyl group as a substituent;

$R_4$ represents a hydrogen atom or a $C_1$-$C_6$ alkyl group; and $R_5$ and $R_6$ are the same or different and each represent a hydrogen atom, a $C_1$-$C_6$ alkyl group, or a $C_3$-$C_6$ cycloalkyl group, or $R_5$ and $R_6$ optionally form a 3 to 6-membered nitrogen-containing saturated heterocyclic group together with a nitrogen atom to which $R_5$ and $R_6$ are bound.

The present invention also provides a drug comprising the piperidine compound represented by the aforementioned general formula (I) or a salt thereof as an active ingredient.

The present invention also provides an aurora A-selective inhibitor, an anti-tumor agent, or an agent for potentiation of anti-tumor effect of a microtubule-targeting agent, comprising the piperidine compound represented by the aforementioned general formula (I) or a salt thereof as an active ingredient.

The present invention also provides use of the piperidine compound represented by the aforementioned general formula (I) or a salt thereof for the production of an aurora A-selective inhibitor, an anti-tumor agent, or an agent for potentiation of anti-tumor effect of a microtubule-targeting agent.

The present invention also provides the piperidine compound represented by the aforementioned general formula (I) or a salt thereof for selective inhibition of aurora A, treatment of cancer, or potentiation of an anti-tumor effect of a microtubule-targeting agent.

The present invention also provides a method for selective inhibition of aurora A, treatment of cancer, or potentiation of an anti-tumor effect of a microtubule-targeting agent, comprising administering an effective dose of the piperidine compound represented by the aforementioned general formula (I) or a salt thereof.

The present invention also provides a cancer therapeutic agent comprising the piperidine compound represented by the aforementioned general formula (I) or a salt thereof and a microtubule-targeting agent; a composition comprising the piperidine compound represented by the aforementioned general formula (I) or a salt thereof and a microtubule-targeting agent for treatment of cancer; use of a composition comprising the piperidine compound represented by the aforementioned general formula (I) or a salt thereof and a microtubule-targeting agent for the production of a cancer treatment drug; and a method for treating cancer, comprising administering an effective dose of the piperidine compound represented by the aforementioned general formula (I) or a salt thereof concomitantly with an effective dose of a microtubule-targeting agent.

The present invention further provides the aforementioned drug, aurora A-selective inhibitor, anti-tumor agent, or agent for potentiation of anti-tumor effect of a microtubule agonist for oral administration; use of the aforementioned aurora A-selective inhibitor, anti-tumor agent, or microtubule-targeting agent for oral administration for the production of an anti-tumor effect potentiator; the aforementioned compound or a salt thereof for the aforementioned aurora A-selective inhibition, treatment of cancer, or potentiation of an anti-tumor effect of a microtubule-targeting agent by oral administration; and a method for the aforementioned aurora A-selective inhibition, treatment of cancer, or potentiation of an anti-tumor effect of a microtubule-targeting agent, wherein administration is done by means of oral administration.

Effects of the Invention

The compound (I) of the present invention or a salt thereof shows an excellent aurora A-selective inhibitory activity and cancer cell proliferation inhibitory activity, and is orally administrable. The compound (I) of the present invention or a salt thereof is useful not only as an anti-tumor agent, but also for administration in combination with microtubule-targeting agents containing a taxane anticancer agent.

DETAILED DESCRIPTION OF THE INVENTION

In the compound (I) of the present invention, selection of $R_2$ is important in terms of the aurora A-selective inhibitory activity, oral absorbability, anti-tumor activity by oral administration, and potentiation of the anti-tumor effect of microtubule-targeting agents containing a taxane anticancer agent. The compound of the present invention is characterized in that $R_2$ is a halogen atom or a $C_1$-$C_6$ alkoxy group.

In the specification of the present application, the "$C_1$-$C_6$ alkyl group" represents a linear or branched alkyl group having 1 to 6 carbon atoms, and specific examples thereof include a methyl group, an ethyl group, an n-propyl group, an isopropyl group, an n-butyl group, an isobutyl group, a sec-butyl group, a tert-butyl group, a pentyl group, and a hexyl group. The $C_1$-$C_6$ alkyl group is preferably a linear or branched alkyl group having 1 to 4 carbon atoms ($C_1$-$C_4$ alkyl group).

In the specification of the present application, the "oxadiazolyl group" refers to a 1,2,4-oxadiazolyl group or a 1,3,4-oxadiazolyl group. The oxadiazolyl ring is preferably unsubstituted or substituted with a $C_1$-$C_4$ alkyl group or a trifluoromethyl group, and the oxadiazolyl ring is more preferably unsubstituted or substituted with a methyl group or a trifluoromethyl group.

In the specification of the present application, examples of the "halogen atom" include a fluorine atom, a chlorine atom, a bromine atom, and an iodine atom.

In the specification of the present application, the "$C_1$-$C_6$ alkoxy group" represents a linear or branched alkoxy group having 1 to 6 carbon atoms, and specific examples thereof include a methoxy group, an ethoxy group, an n-propoxy group, an isopropoxy group, an n-butoxy group, an isobutoxy group, a t-butoxy group, a pentoxy group, and a hexoxy group. The $C_1$-$C_6$ alkoxy group is preferably a linear or branched alkoxy group having 1 to 4 carbon atoms ($C_1$-$C_4$ alkoxy group).

In the specification of the present application, the "$C_3$-$C_6$ cycloalkyl group" refers to a monocyclic cycloalkyl group having 3 to 6 carbon atoms, and specific examples thereof include a cyclopropyl group, a cyclobutyl group, a cyclopentyl group, and a cyclohexyl group. The $C_3$-$C_6$ cycloalkyl group is preferably a cyclopropyl group or a cyclobutyl group.

In the specification of the present application, the phrase "$R_5$ and $R_6$ optionally form a 3 to 6-membered nitrogen-containing saturated heterocyclic group together with a nitrogen atom to which $R_5$ and $R_6$ are bound" means that $R_5$ and $R_6$ optionally form, together with a nitrogen atom to which $R_5$ and $R_6$ are bound (that is, as —$NR_5R_6$), a 3 to 6-membered saturated heterocyclic group further containing 0 to 2 nitrogen atom(s) and/or oxygen atom(s) within the ring. Specific examples of the 3 to 6-membered nitrogen-containing saturated heterocyclic group which is optionally formed include an azetidinyl group, a pyrrolidinyl group, a piperidinyl group, a piperazinyl group, a morpholinyl group, and an isoxazolidinyl group.

In the general formula (I), $R_1$ is preferably a carboxyl group, —C(=O)$NR_5R_6$ (wherein, $R_5$ and $R_6$ are the same or different and each represent a hydrogen atom, a $C_1$-$C_6$ alkyl group, or a $C_3$-$C_6$ cycloalkyl group, or $R_5$ and $R_6$ optionally form an azetidinyl group, a pyrrolidinyl group, or an isoxazolidinyl group together with a nitrogen atom to which $R_5$ and $R_6$ are bound), or an oxadiazolyl group optionally having a $C_1$-$C_6$ alkyl group or a trifluoromethyl group as a substituent.

In the general formula (I), $R_1$ is more preferably a carboxyl group, —C(=O)$NR_5R_6$ (wherein, $R_5$ and $R_6$ are the same or different and each represent a hydrogen atom, a methyl group, a cyclopropyl group, or a cyclobutyl group, or $R_5$ and $R_6$ represent an azetidinyl group, a pyrrolidinyl group, or an isoxazolidinyl group together with a nitrogen atom to which $R_5$ and $R_6$ are bound), or an oxadiazolyl group optionally having a methyl group or a trifluoromethyl group as a substituent.

As demonstrated in Examples later, it is important that $R_2$ in the general formula (I) be a halogen atom or a $C_1$-$C_6$ alkoxy group in terms of the aurora A-selective inhibitory activity, oral absorbability, anti-tumor activity by oral administration, and a potentiation of the anti-tumor effect of microtubule-targeting agents including a taxane anticancer agent. The $R_2$ is preferably a fluorine atom, a chlorine atom, or a $C_1$-$C_4$ alkoxy group, more preferably a fluorine atom, a chlorine atom, or a methoxy group.

In the general formula (I), $R_3$ is preferably a phenyl group optionally having 1 to 3 same or different group(s) selected from a halogen atom, a $C_1$-$C_4$ alkyl group, a $C_1$-$C_4$ alkoxy group, and a trifluoromethyl group as a substituent, more preferably a phenyl group having 1 to 2 same or different group(s) selected from the aforementioned substituents. $R_3$ is even more preferably a phenyl group having 1 to 2 same or different group(s) selected from a fluorine atom, a chlorine atom, a methyl group, a methoxy group, and a trifluoromethyl group as a substituent.

In the general formula (I), $R_4$ is preferably a hydrogen atom or a $C_1$-$C_4$ alkyl group, and more preferably a hydrogen atom or a methyl group.

In the compound of the present invention, it is preferable that $R_1$ is a carboxyl group, —C(=O)$NR_5R_6$ (wherein, $R_5$ and $R_6$ are the same or different and each represent a hydrogen atom, a $C_1$-$C_4$ alkyl group, or a $C_3$-$C_6$ cycloalkyl group, or $R_5$ and $R_6$ optionally form an azetidinyl group, a pyrrolidinyl group, or an isoxazolidinyl group together with a nitrogen atom to which $R_5$ and $R_6$ are bound), or an oxadiazolyl group optionally having a $C_1$-$C_4$ alkyl group or a trifluoromethyl group as a substituent; $R_2$ is a fluorine atom, a chlorine atom, or a $C_1$-$C_4$ alkoxy group; $R_3$ is a phenyl group optionally having 1 to 2 same or different group(s) selected from a halogen atom, a $C_1$-$C_4$ alkyl group, a $C_1$-$C_4$ alkoxy group, and a trifluoromethyl group as a substituent; and $R_4$ is a hydrogen atom or a $C_1$-$C_4$ alkyl group.

Also, as the compound of the present invention, a compound in which, in the general formula (I), $R_1$ is a carboxyl group, —C(=O)$NR_5R_6$ (wherein, $R_5$ and $R_6$ are the same or different and each represent a hydrogen atom, a methyl group, a cyclopropyl group, or a cyclobutyl group, or $R_5$ and $R_6$ represent an azetidinyl group, a pyrrolidinyl group, or an isoxazolidinyl group together with a nitrogen atom to which $R_5$ and $R_6$ are bound), or an oxadiazolyl group optionally having a methyl group or a trifluoromethyl group as a substituent; $R_2$ is a fluorine atom, a chlorine atom, or a methoxy group; $R_3$ is a phenyl group optionally having 1 to 2 same or different group(s) selected from a fluorine atom, a chlorine atom, a methyl group, a methoxy group, and a trifluoromethyl group as a substituent; and $R_4$ is a hydrogen atom or a methyl group is preferable.

Also, a compound in which $R_1$ is a carboxyl group, —C(=O)$NR_5R_6$ (wherein, $R_5$ and $R_6$ are the same or different and each represent a hydrogen atom or a methyl group, or $R_5$ and $R_6$ represent an isoxazolidinyl group together with a nitrogen atom to which $R_5$ and $R_6$ are bound), or a 1,2,4-oxadiazolyl group or a 1,3,4-oxadiazolyl group optionally having a methyl group as a substituent; $R_2$ is a fluorine atom, a chlorine atom, or a methoxy group; $R_3$ is a phenyl group having 1 to 2 same or different group(s) selected from a fluorine atom, a chlorine atom, a methyl group, a methoxy group, and a trifluoromethyl group as a substituent; and $R_4$ is a hydrogen atom or a methyl group is more preferable.

Further, a compound in which $R_1$ is a carboxyl group or a 1,2,4-oxadiazolyl group optionally having a methyl group as a substituent; $R_2$ is a fluorine atom; $R_3$ is a phenyl group having 1 to 2 same or different group(s) selected from a fluorine atom and a chlorine atom as a substituent; and $R_4$ is a methyl group is particularly preferable.

The following compounds can be given as examples of specific preferable compounds of the present invention.

1-(2,3-dichlorobenzoyl)-4-((5-fluoro-6-(5-methyl-1H-pyrazol-3-ylamino)pyridin-2-yl)methyl)piperidine-4-carboxylic acid (compound 1)

1-(2-fluoro-3-trifluoromethylbenzoyl)-4-((5-fluoro-6-(5-methyl-1H-pyrazol-3-ylamino)pyridin-2-yl)methyl)piperidine-4-carboxylic acid (compound 2)

1-(3-chloro-2-fluorobenzoyl)-4-((5-fluoro-6-(1H-pyrazol-3-ylamino)pyridin-2-yl)methyl)piperidine-4-carboxylic acid (compound 10)

1-(3-chloro-2-fluorobenzoyl)-4-((5-methoxy-6-(5-methyl-1H-pyrazol-3-ylamino)pyridin-2-yl)methyl)piperidine-4-carboxylic acid (compound 11)

1-(3-chloro-2-fluorobenzoyl)-4-((5-chloro-6-(5-methyl-1H-pyrazol-3-ylamino)pyridin-2-yl)methyl)piperidine-4-carboxylic acid (compound 12)

1-(3-chloro-2-fluorobenzoyl)-4-((5-fluoro-6-(5-methyl-1H-pyrazol-3-ylamino)pyridin-2-yl)methyl)piperidine-4-carboxylic acid (compound 13)

1-(3-chloro-2-fluorobenzoyl)-4-((5-fluoro-6-(5-methyl-1H-pyrazol-3-ylamino)pyridin-2-yl)methyl)-N-methylpiperidine-4-carboxamide (compound 14)

1-(3-chloro-2-fluorobenzoyl)-4-((5-fluoro-6-(5-methyl-1H-pyrazol-3-ylamino)pyridin-2-yl)methyl)-N,N-dimethylpiperidine-4-carboxamide (compound 16)

azetidin-1-yl(1-(3-chloro-2-fluorobenzoyl)-4-((5-fluoro-6-(5-methyl-1H-pyrazol-3-ylamino)pyridin-2-yl)methyl)piperidin-4-yl)methanone (compound 19)

(1-(3-chloro-2-fluorobenzoyl)-4-((5-fluoro-6-(5-methyl-1H-pyrazol-3-ylamino)pyridin-2-yl)methyl)piperidin-4-yl) (isoxazolidin-2-yl)methanone (compound 21)

(3-chloro-2-fluorophenyl) (4-((5-fluoro-6-(5-methyl-1H-pyrazol-3-ylamino)pyridin-2-yl)methyl)-4-(5-methyl-1,2,4-oxadiazol-3-yl)piperidin-1-yl)methanone (compound 22)

(2,3-dichlorophenyl)(4-((5-fluoro-6-(5-methyl-1H-pyrazol-3-ylamino)pyridin-2-yl)methyl)-4-(5-methyl-1,2,4-oxadiazol-3-yl)piperidin-1-yl)methanone (compound 23)

(3-chloro-2-fluorophenyl) (4-((5-fluoro-6-(5-methyl-1H-pyrazol-3-ylamino)pyridin-2-yl)methyl)-4-(1,2,4-oxadiazol-3-yl)piperidin-1-yl)methanone (compound 24)

(3-chloro-2-fluorophenyl) (4-((5-fluoro-6-(5-methyl-1H-pyrazol-3-ylamino)pyridin-2-yl)methyl)-4-(5-methyl-1,3,4-oxadiazol-3-yl)piperidin-1-yl)methanone (compound 28)

(3-chloro-2-fluorophenyl) (4-((5-fluoro-6-(5-methyl-1H-pyrazol-3-ylamino)pyridin-2-yl)methyl)-4-(3-methyl-1,2,4-oxadiazol-5-yl)piperidin-1-yl)methanone (compound 29)

Next, a representative production method of the compound (I) of the present invention is hereinafter illustrated.

The compound (I) of the present invention can be produced by, for example, the following production method, a method shown in Examples. However, the production method of the compound (I) of the present invention is not limited to these reaction examples. The raw materials necessary for the synthesis of the compound of the present invention can be obtained as commercial products or easily produced by a production method described in, for example, prior art documents.

Among the compounds (I) of the present invention, a compound (I-1), in which $R_1$ is a carboxyl group, can be produced by, for example, the following production method 1.

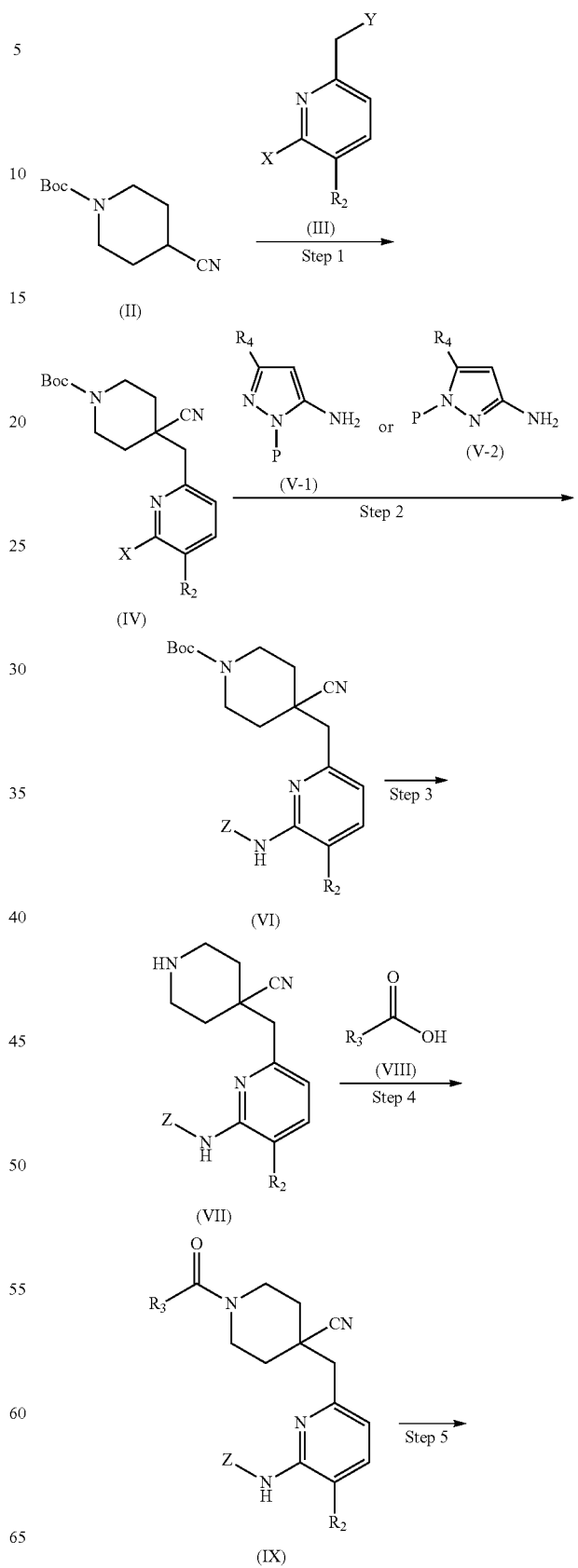

Production method 1

-continued

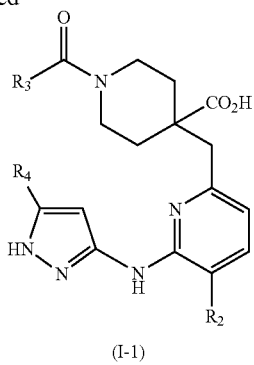

(I-1)

wherein, X and Y each represent a leaving group; P represents a hydrogen atom or a protecting group; and Z represents a general formula (a) or (b):

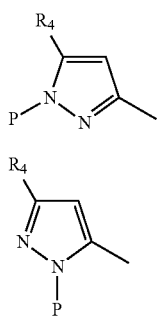

and $R_2$, $R_3$, and $R_4$ are defined as above.

In the above production method 1, examples of the leaving group represented by X or Y include a halogen atom, and it is preferably a bromine atom. Examples of the protecting group represented by P include a tert-butyl group, a methoxy methyl group, a [(2-trimethylsilyl)ethoxy]methyl group, and a benzyl group, and it is preferably a tert-butyl group.

(Step 1)

This step is a method for producing a compound (IV) by reacting a compound (II) with a base, and then with a compound (III). Examples of the compound (III) to be used in this step include 6-bromo-2-bromomethyl-5-fluoropyridine, 6-bromo-2-chloromethyl-5-fluoropyridine, 2-bromomethyl-6-chloro-5-fluoropyridine, 2-bromomethyl-5,6-dichloropyridine, and 6-bromo-2-bromomethyl-5-methoxypyridine, and it is preferably 6-bromo-2-bromomethyl-5-fluoropyridine. The compound (III) can be obtained as a commercial product or produced in accordance with a publicly known method.

The amount of the compound (III) to be used in this step is 0.1 to 10 equivalents, preferably 0.8 to 2 equivalents relative to one equivalent of compound (II). The reaction temperature is −90 to 100° C., preferably −78 to 0° C. The reaction time is 0.1 to 100 hours, preferably 0.5 to 10 hours. Examples of the base include lithium diisopropylamine and lithium hexamethyldisilazide, and the base can be used in an amount of 0.5 to 10 equivalents, preferably 1 to 1.5 equivalents. The solvent to be used in this reaction is not particularly limited as long as it does not interfere with the reaction, and examples thereof include tetrahydrofuran, 2-methyltetrahydrofuran, diethyl ether, 1,2-dimethoxyethane, and toluene. These solvents can be used alone or as a mixture thereof.

The compound (IV) to be obtained as above can be subjected to the subsequent step with or without isolation and purification by a publicly known isolation and purification methods such as concentration, concentration under reduced pressure, crystallization, solvent extraction, reprecipitation, and chromatography.

(Step 2)

This step is a method for producing a compound (VI) by a coupling reaction between the compound (IV) and a compound (V). Examples of the compound (V) to be used in this step (compound (V-1) or compound (V-2)) include 1-tert-butyl-3-methyl-1H-pyrazol-5-amine, 1-tert-butyl-1H-pyrazol-5-amine, 1-{[2-(trimethylsilyl)ethoxy]methyl}-1H-pyrazol-3-amine, and 5-methyl-1-{[2-(trimethylsilyl)ethoxy]methyl}-1H-pyrazol-3-amine. The compound (V) can be obtained as a commercial product or produced in accordance with a publicly known method.

The amount of the compound (V) to be used in this step is 0.5 to 10 equivalents, preferably 0.8 to 2 equivalents relative to one equivalent of compound (IV). Examples of a catalyst to be used include a metal catalyst such as tris (benzylideneacetone)dipalladium and palladium acetate, and the catalyst can be used in an amount of 0.001 to 5 equivalents, preferably 0.005 to 0.1 equivalent relative to one equivalent of compound (IV). Examples of a ligand for the aforementioned metal catalyst include 4,5-bis(diphenylphosphino)-9,9-dimethylxanthene and 2,2'-bisdiphenylphosphino-1,1'-binaphthyl, and these ligands can be used in an amount of 0.001 to 5 equivalents, preferably 0.005 to 0.2 equivalent relative to one equivalent of compound (IV). The reaction temperature is 0 to 200° C., preferably room temperature to 130° C. The reaction time is 0.1 to 100 hours, preferably 0.5 to 20 hours. Examples of the base include an inorganic base such as potassium phosphate, sodium carbonate, potassium carbonate, cesium carbonate, and sodium tert-butoxide, and organic amines such as trimethylamine, diisopropylethylamine, and pyridine, and these bases can be used in an amount of 0.5 to 10 equivalents, preferably 1 to 3 equivalents. The solvent to be used in this reaction is not particularly limited as long as it does not interfere with the reaction, and examples thereof include toluene, tetrahydrofuran, dioxane, N,N-dimethylformamide, N,N-dimethylacetamide, N-methylpyrrolidin-2-one, tert-butanol, and tert-amyl alcohol. These solvents can be used alone or as a mixture thereof.

The compound (VI) to be obtained as above can be subjected to the subsequent step with or without isolation and purification by a publicly known isolation and purification methods such as concentration, concentration under reduced pressure, crystallization, solvent extraction, reprecipitation, and chromatography.

(Step 3)

This step is a method for producing a compound (VII) by removing the tert-butoxycarbonyl group, which is the protecting group for the compound (VI), in the presence of an acid. With regard to the reaction conditions used in this step, this step can be carried out in accordance with the method described in the Document (Protective Groups in Organic Synthesis, written by T. W. Greene, John Wiley & Sons, Inc. (1981)) or a method equivalent to the above method. Examples of the acid to be used include trifluoroacetic acid, hydrochloric acid, sulfuric acid, methanesulfonic acid, and toluenesulfonic acid, and the acid can be used in an amount of 0.1 to 100 equivalents, preferably 1 to 10 equivalents. The reaction temperature is 0 to 200° C., preferably room temperature to 100° C. The reaction time is 0.1 to 100 hours, preferably 0.5 to 20 hours. The solvent to be used in this reaction is not particularly limited as long as it does not interfere with the reaction, and examples thereof include chloroform, acetonitrile, toluene, tetrahydrofuran, dioxane, water, and acetic acid. These solvents can be used alone or as a mixture thereof.

The compound (VII) to be obtained as above can be subjected to the subsequent step with or without isolation and purification by a publicly known isolation and purification methods such as concentration, concentration under reduced pressure, crystallization, solvent extraction, reprecipitation, and chromatography.

(Step 4)

This step is a reaction for obtaining a compound (IX) by a dehydration condensation reaction between the compound (VII) and a compound (VIII). Examples of the compound (VIII) to be used in this step include 2-fluoro-3-chlorobenzoic acid and 2,3-dichlorobenzoic acid. The compound (VIII) can be obtained as a commercial product or produced in accordance with a publicly known method. In this step, using a commonly used condensing agent, the compound (IX) can be obtained in accordance with a publicly known method. Examples of the condensing agent include N,N'-dicyclohexylcarbodiimide (DCC), N,N'-diisopropylcarbodiimide (DIC), 1-ethyl-3-(3-dimethylaminopropyl)carbodiimide hydrochloride (WSC), diphenylphosphoryl azide (DPPA), (benzotriazol-1-yl-oxy) trisdimethylaminophosphonium hexafluorophosphate (BOP), (benzotriazol-1-yl-oxy) tripyrrolidinophosphonium hexafluorophosphate (PyBOP), (7-azabenzotriazol-1-yloxy) trispyrrolidinophosphonium phosphate (PyAOP), bromotrispyrrolidinophosphonium hexafluorophosphate (BroP), chlorotris(pyrrolidin-1-yl)phosphonium hexafluorophosphate (PyCroP), 3-(diethoxyphosphoryloxy)-1,2,3-benzotriazin-4(3H)-one (DEPBT), O-(benzotriazol-1-yl)-N,N,N',N'-tetramethyluronium hexafluorophosphate (HATU), and 4-(5,6-dimethoxy-1,3,5-triazin-2-yl)-4-methylmorpholine hydrochloride (DMTMM). Examples of an additive to be used in this step include 1-hydroxybenzotriazol (HOBt), 1-hydroxy-7-azabenzotriazole (HOAt), and N-hydroxysuccinimide (HOSu). These additives can be used in an amount of 0.1 to 100 equivalents, preferably 1 to 10 equivalents. If necessary, a base such as trimethylamine, triethylamine, tripropylamine, diisopropylethylamine, N-methylmorpholine, pyridine, 4-(N,N-dimethylamino)pyridine, lutidine, and collidine can be used in an amount of 0.1 to 100 equivalents, preferably 1 to 10 equivalents. The solvent is not particularly limited, and for example, water, methanol, ethanol, 2-propanol, tetrahydrofuran, 1,4-dioxane, toluene, methylene chloride, chloroform, acetonitrile, N,N-dimethylformamide, and N,N-dimethylacetamide, dimethyl sulfoxide can be used. The reaction temperature is −30 to 200° C., preferably 0 to 50° C. The reaction time is 0.1 to 100 hours, preferably 0.5 to 24 hours.

The compound (IX) to be obtained as above can be subjected to the subsequent step with or without isolation and purification by a publicly known isolation and purification methods such as concentration, concentration under reduced pressure, crystallization, solvent extraction, reprecipitation, and chromatography.

(Step 5)

This step is a method for producing a compound (I-1) by simultaneously carrying out hydrolysis of the cyano group of the compound (IX) and removal of the protecting group (P) of the substituent Z under the acidic conditions. Examples of an acid to be used include hydrochloric acid, sulfuric acid, methanesulfonic acid, toluenesulfonic acid, and trifluoroacetic acid. These acids can be used in an amount of 0.1 to 100 equivalents, preferably 1 to 10 equivalents. The reaction temperature is room temperature to 200° C., preferably 60 to 130° C. The reaction time is 0.1 to 100 hours, preferably 0.5 to 20 hours. The solvent to be used in this reaction is not particularly limited as long as it does not interfere with the reaction, and examples thereof include dioxane, water, acetic acid, toluene, tetrahydrofuran, and 2-propanol. These solvents can be used alone or as a mixture thereof. The compound (I-1) to be obtained as above can be isolated and purified by a publicly known isolation and purification methods such as concentration, concentration under reduced pressure, crystallization, solvent extraction, reprecipitation, and chromatography.

Among the compounds of the general formula (I), a compound (I-2), in which $R_1$ is —C(=O)NR$_5$R$_6$, can be produced by, for example, the following production method 2.

Production method 2

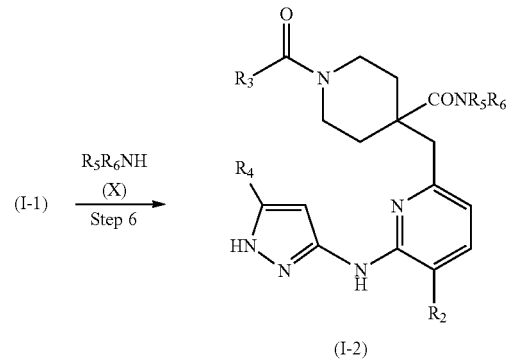

wherein, $R_2$, $R_3$, $R_4$, $R_5$, and $R_6$ are defined as above.

(Step 6)

This step is a method for producing the compound (I-2) by a dehydration condensation reaction between the compound (I-1) obtained by the production method 1 and a compound (X). Examples of the compound (X) to be used in this step include an amine such as methylamine, dimethylamine, ammonium chloride, cyclopropylamine, and pyrrolidine as well as salts thereof. The compound (X) can be obtained as a commercial product or produced in accordance with a publicly known method. In this step, using a commonly used condensing agent, the compound (I-2) can be obtained in accordance with a publicly known method. Examples of the condensing agent include N,N'-dicyclohexylcarbodiimide (DCC), N,N'-diisopropylcarbodiimide (DIC), 1-ethyl-3-(3-dimethylaminopropyl)carbodiimide hydrochloride (WSC), diphenylphosphoryl azide (DPPA), (benzotriazol-1-yl-oxy) trisdimethylaminophosphonium hexafluorophosphate (BOP), (benzotriazol-1-yl-oxy) tripyrrolidinophosphonium hexafluorophosphate (PyBOP), (7-azabenzotriazol-1-yloxy) trispyrrolidinophosphonium phosphate (PyAOP), bromotrispyrrolidinophosphonium hexafluorophosphate (BroP), chlorotris(pyrrolidin-1-yl)phosphonium hexafluorophosphate (PyCroP), 3-(diethoxyphosphoryloxy)-1,2,3-benzotriazin-4(3H)-one (DEPBT), O-(benzotriazol-1-yl)-N,N,N',N'-tetramethyluronium hexafluorophosphate (HATU), and 4-(5,6-dimethoxy-1,3,5-triazin-2-yl)-4-methylmorpholine hydrochloride (DMTMM). Examples of an additive to be used in this step include 1-hydroxybenzotriazol (HOBt), 1-hydroxy-7-azabenzotriazole (HOAt), and N-hydroxysuccinimide (HOSu). These additives can be used in an amount of 0.1 to 100 equivalents, preferably 1 to 10 equivalents. If necessary, a base such as trimethylamine, triethylamine, tripropylamine, diisopropylethylamine, N-methylmorpholine, pyridine, 4-(N,N-dimethylamino)pyridine, lutidine, and collidine can be used in an amount of 0.1 to 100 equivalents, preferably 1 to 10 equivalents. The solvent is not particularly limited, and for example, water, methanol, ethanol, 2-propanol, tetrahydrofuran, 1,4-dioxane, toluene, methylene chloride, chloroform, acetonitrile, N,N-dimethylformamide, N,N-dimethylacetamide, and dimethyl sulfoxide can be used. The reaction temperature is −30 to 200° C., preferably 0 to 50° C. The reaction time is 0.1 to 100 hours, preferably 0.5 to 24 hours.

The compound (I-2) to be obtained as above can be isolated and purified by a publicly known isolation and purification methods such as concentration, concentration under reduced pressure, crystallization, solvent extraction, reprecipitation, and chromatography.

Among the compounds of the general formula (I), a compound (I-3), in which $R_1$ is 1,2,4-oxadiazol substituted with $R_7$, can be produced by, for example, the following production method 3.

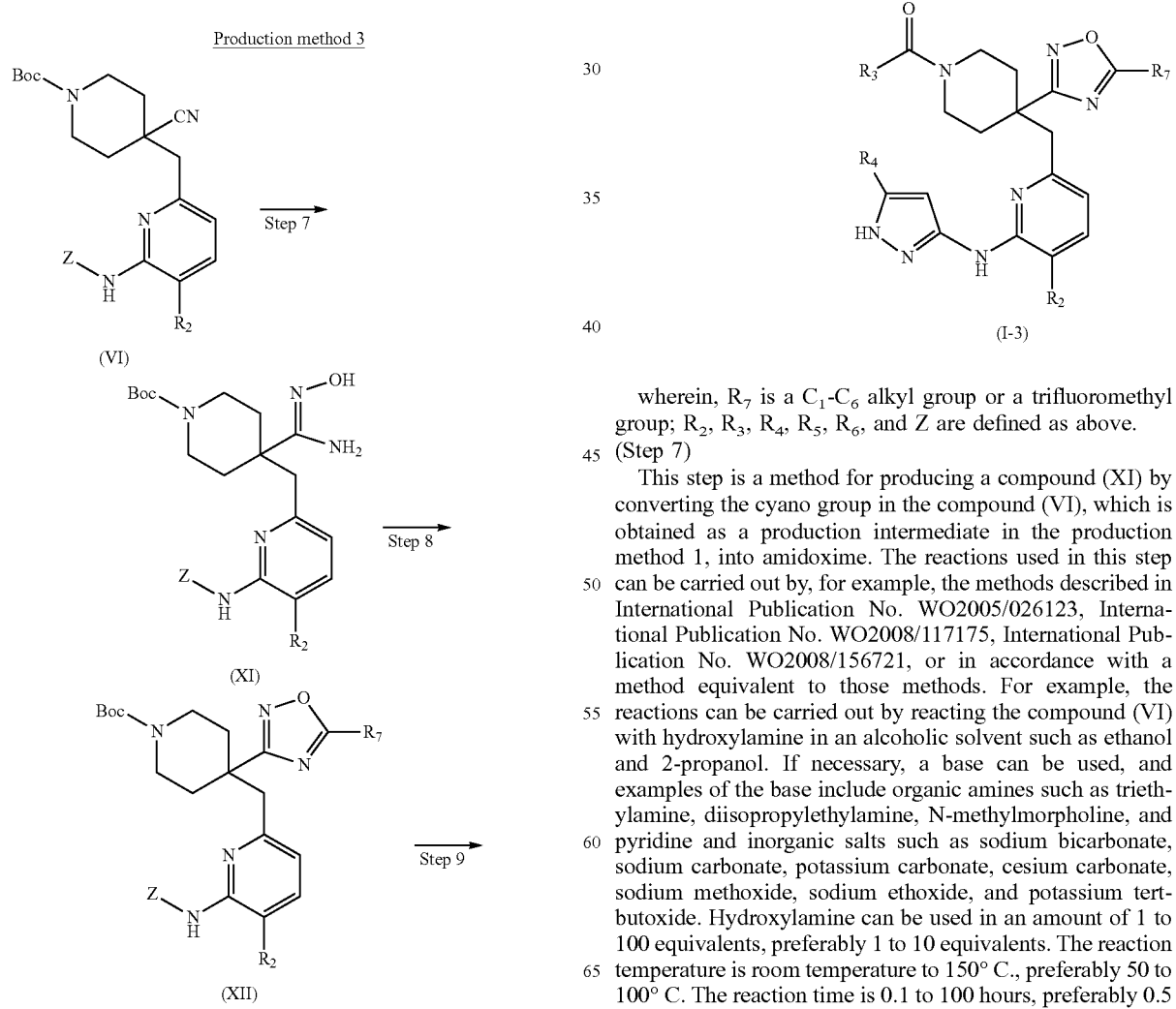

wherein, $R_7$ is a $C_1$-$C_6$ alkyl group or a trifluoromethyl group; $R_2$, $R_3$, $R_4$, $R_5$, $R_6$, and Z are defined as above.

(Step 7)

This step is a method for producing a compound (XI) by converting the cyano group in the compound (VI), which is obtained as a production intermediate in the production method 1, into amidoxime. The reactions used in this step can be carried out by, for example, the methods described in International Publication No. WO2005/026123, International Publication No. WO2008/117175, International Publication No. WO2008/156721, or in accordance with a method equivalent to those methods. For example, the reactions can be carried out by reacting the compound (VI) with hydroxylamine in an alcoholic solvent such as ethanol and 2-propanol. If necessary, a base can be used, and examples of the base include organic amines such as triethylamine, diisopropylethylamine, N-methylmorpholine, and pyridine and inorganic salts such as sodium bicarbonate, sodium carbonate, potassium carbonate, cesium carbonate, sodium methoxide, sodium ethoxide, and potassium tert-butoxide. Hydroxylamine can be used in an amount of 1 to 100 equivalents, preferably 1 to 10 equivalents. The reaction temperature is room temperature to 150° C., preferably 50 to 100° C. The reaction time is 0.1 to 100 hours, preferably 0.5 to 20 hours.

The compound (XI) to be obtained as above can be subjected to the subsequent step with or without isolation and purification by a publicly known isolation and purification methods such as concentration, concentration under reduced pressure, crystallization, solvent extraction, reprecipitation, and chromatography.

(Step 8)

This step is a method for producing a compound (XII) by converting the amidoxime group in the compound (XI) into a 1,2,4-oxadiazole ring. The reactions used in this step can be carried out by, for example, the methods described in International Publication No. WO2005/026123, International Publication No. WO2008/117175, International Publication No. WO2008/156721, or in accordance with a method equivalent to those methods. For example, the reactions can be carried out by reacting the compound (XI) with acetic anhydride, acetyl chloride, triethyl orthoformate, and triethyl orthoacetate in a solvent such as toluene, chloroform, acetic acid, N,N-dimethylformamide, N-methylpyrrolidin-2-one, and pyridine. If necessary, a base can be used, and examples of the base include triethylamine, diisopropylethylamine, N-methylmorpholine, and pyridine. The reaction temperature is room temperature to 150° C., preferably 50 to 100° C. The reaction time is 0.1 to 100 hours, preferably 0.5 to 20 hours.

The compound (XII) to be obtained as above can be subjected to the subsequent step with or without isolation and purification by a publicly known isolation and purification methods such as concentration, concentration under reduced pressure, crystallization, solvent extraction, reprecipitation, and chromatography.

(Step 9)

This step is a method for producing a compound (XIII) by removing the tert-butoxycarbonyl group, which is the protecting group for the compound (XII), in the presence of an acid. This step can be carried out by a method similar to that used in the aforementioned step 3 or a method equivalent to that used in the step 3.

The compound (XIII) to be obtained as above can be subjected to the subsequent step with or without isolation and purification by a publicly known isolation and purification methods such as concentration, concentration under reduced pressure, crystallization, solvent extraction, reprecipitation, and chromatography.

(Step 10)

This step is a method for producing a compound (XIV) by a dehydration condensation reaction between the compound (XIII) and the compound (VIII). This step can be carried out by a method similar to that used in the aforementioned step 4 or a method equivalent to that used in the step 4.

The compound (XIV) to be obtained as above can be subjected to the subsequent step with or without isolation and purification by a publicly known isolation and purification methods such as concentration, concentration under reduced pressure, crystallization, solvent extraction, reprecipitation, and chromatography.

(Step 11)

This step is a method for producing a compound (I-3) by removing the protecting group (P) of the substituent Z in the compound (XIV) in the presence of an acid. This step can be carried out by a method similar to that used in the aforementioned step 5 or a method equivalent to that used in the step 5.

The compound (I-3) to be obtained as above can be isolated and purified by a publicly known isolation and purification methods such as concentration, concentration under reduced pressure, crystallization, solvent extraction, reprecipitation, and chromatography.

Among the compounds of the general formula (I), a compound (I-4), in which $R_1$ is 1,3,4-oxadiazol substituted with $R_7$, can be produced by, for example, the following production method 4.

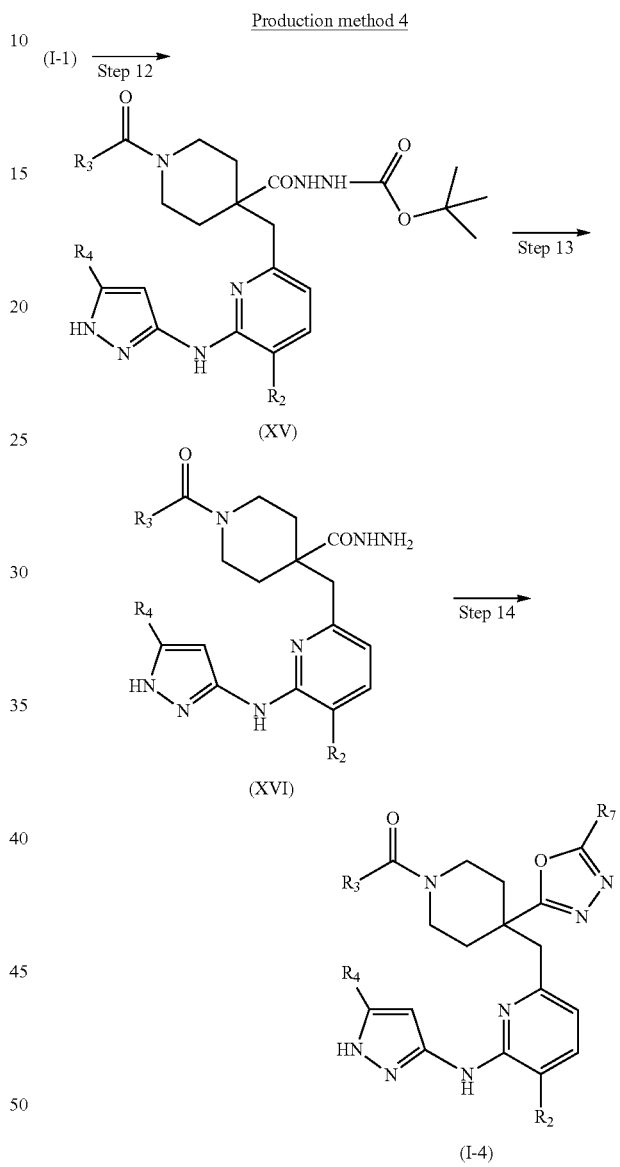

wherein, $R_7$ represents a $C_1$-$C_6$ alkyl group or a trifluoromethyl group; $R_2$, $R_3$, and $R_4$ are defined as above.

(Step 12)

This step is a method for producing a compound (XV) by a dehydration condensation reaction between the compound (I-1) obtained by the production method 1 and tert-butoxycarbonyl hydrazide. This step can be carried out by a method similar to that used in the aforementioned step 4 or a method equivalent to that used in the step 4.

The compound (XV) to be obtained as above can be subjected to the subsequent step with or without isolation and purification by a publicly known isolation and purification methods such as concentration, concentration under reduced pressure, crystallization, solvent extraction, reprecipitation, and chromatography.

(Step 13)

This step is a method for producing a compound (XVI) by removing the tert-butoxycarbonyl group, which is the protecting group for the compound (XV), in the presence of an acid. This step can be carried out by a method similar to that used in the aforementioned step 3 or a method equivalent to that used in the step 3.

The compound (XVI) to be obtained as above can be subjected to the subsequent step with or without isolation and purification by a publicly known isolation and purification methods such as concentration, concentration under reduced pressure, crystallization, solvent extraction, reprecipitation, and chromatography.

(Step 14)

This step is a method for producing a compound (I-4) by converting the acyl hydrazide group in the compound (XVI) into a 1,3,4-oxadiazole ring. This step can be carried out by a method similar to that used in the aforementioned step 8 or a method equivalent to that used in the step 8.

The compound (I-4) to be obtained as above can be subjected to the subsequent step with or without isolation and purification by a publicly known isolation and purification methods such as concentration, concentration under reduced pressure, crystallization, solvent extraction, reprecipitation, and chromatography.

When the compound of the present invention includes isomers such as optical isomers, stereoisomers, position isomers, and rotational isomers, a mixture of any isomer is also encompassed by the compound of the present invention. For example, when optical isomers exist for the compound of the present invention, the optical isomers which are separated from racemic forms are also encompassed by the compound of the present invention. These isomers can be individually obtained as a single compound by a synthetic technique or separation technique known per se (such as concentration, solvent extraction, column chromatography, and recrystallization).

The compound of the present invention or a salt thereof may be a crystal, and a single crystal form as well as a polymorphic mixture is encompassed by the compound of the present invention or a salt thereof. A crystal can be produced by carrying out crystallization by applying a crystallization method known per se. The compound of the present invention or a salt thereof may be a solvate (such as a hydrate) or a non-solvate, and both of which are encompassed by the compound of the present invention or a salt thereof. A compound labeled with, for example, an isotope (for example, $^2H$, $^3H$, $^{13}C$, $^{14}C$, $^{18}F$, $^{35}S$, and $^{125}I$) is also encompassed by the compound of the present invention or a salt thereof.

The salt of the compound of the present invention refers to a common salt used in the field of organic chemistry, and examples thereof include salts such as, when a compound has a carboxyl group, a base addition salt of the carboxyl group, and when a compound has an amino group or a basic heterocyclic group, an acid addition salt of the amino group or the basic heterocyclic group.

Examples of the base addition salt include an alkali metal salt such as a sodium salt and a potassium salt; an alkaline earth metal salt such as a calcium salt and a magnesium salt; an ammonium salt; and an organic amine salt such as a trimethylamine salt, a triethylamine salt, a dicyclohexylamine salt, an ethanolamine salt, a diethanolamine salt, a triethanolamine salt, a procaine salt, and an N,N'-dibenzylethylenediamine salt.

Examples of the acid addition salt include an inorganic acid salt such as a hydrochloride, a sulfate, a nitrate, a phosphate, and a perchlorate; an organic acid salt such as an acetate, a formate, a maleate, a fumarate, a tartrate, a citrate, an ascorbate, and a trifluoroacetate; and a sulfonate such as a methanesulfonate, an isethionate, a benzenesulfonate, and a p-toluenesulfonate.

The compound of the present invention or a salt thereof shows an excellent selective aurora A inhibitory activity, and in particular, shows an extremely stronger selective aurora A inhibitory activity compared to the inhibitory activity on aurora B and aurora C, and thus is useful as an aurora A-selective inhibitor. Further, the compound of the present invention or a salt thereof shows an excellent anti-tumor effect, and thus is useful as an anti-tumor agent. Although cancer to be treated is not particularly limited, examples thereof include head and neck cancer, esophageal cancer, stomach cancer, duodenal cancer, colon cancer, rectal cancer, liver cancer, gallbladder and bile duct cancer, biliary tract cancer, pancreatic cancer, lung cancer, breast cancer, ovary cancer, uterine cervical cancer, uterine cancer, renal cancer, bladder cancer, prostate cancer, testicular cancer, bone and soft tissue sarcoma, hematologic cancer, multiple myeloma, skin cancer, brain tumor, mesothelioma, and hematologic cancer. Preferably, cancer to be treated is hematologic cancer such as B cell lymphoma, chronic lymphocytic leukemia, peripheral T-cell lymphoma, myelodysplastic syndrome, acute myelogenous leukemia, acute lymphocytic leukemia, and multiple myeloma, stomach cancer, breast cancer, prostate cancer, ovary cancer, lung cancer, and colon cancer. Additionally, the drug of the present invention can be applied to humans and animals other than humans.

Also, given that the compound of the present invention or a salt thereof has an excellent aurora A-selective inhibitory activity, when it is used in combination with a microtubule-targeting agent, it potentiates the anti-tumor effect of the microtubule-targeting agent. Therefore, the compound of the present invention or a salt thereof is useful as an anti-tumor effect potentiator for a microtubule-targeting agent. A composition containing the compound of the present invention or a salt thereof and a microtubule agonist is useful as an anti-tumor agent (cancer treatment drug). Combinational administration of the compound of the present invention or a salt thereof and a microtubule-targeting agent is useful as a method for treating cancer. Examples of the microtubule-targeting agent include a microtubule stabilizing drug such as a taxane anticancer agent and an epothilone anticancer agent, and preferably, the microtubule-targeting agent is a taxane anticancer agent. Examples of the taxane anticancer agent include paclitaxel, docetaxel, and cabazitaxel, and preferably, the taxane anticancer agent is paclitaxel. Examples of the epothilone anticancer agent include epothilone B and epothilone D. The anti-tumor effect potentiator of the present invention can be administered at any time, i.e., before, or after, or simultaneously with the administration of the microtubule-targeting agent. Preferably, the anti-tumor effect potentiator of the present invention may be administered at the same time with, or within four hours before or after administration of the microtubule-targeting agent. When the anti-tumor effect potentiator of the present invention is administered separately from or simultaneously with the microtubule agonist, for example, the anti-tumor effect potentiator may be administered in such an amount that the amount of at least one component selected from the compounds of the present invention or salts thereof is in a range of 0.01 to 100 moles, preferably 0.05 to 50 moles, more preferably 0.1 to 20 moles relative to one mole of the microtubule-targeting agent. Although cancer to be treated is not particularly limited, examples thereof include head and neck cancer, esophageal cancer, stomach cancer, duodenal cancer, colon cancer, rectal cancer, liver cancer, gallbladder and bile duct cancer, biliary tract cancer, pancreatic cancer, lung cancer, breast cancer, ovary cancer, uterine cervical cancer, uterine cancer, renal cancer, bladder cancer, prostate cancer, testicular cancer, bone and soft tissue sarcoma, hematologic cancer, multiple myeloma, skin cancer, brain tumor, mesothelioma, and hematologic cancer. Preferably, cancer to be treated is hematologic cancer such as B cell lymphoma, chronic lymphocytic leukemia, peripheral T-cell lymphoma, myelodysplastic syndrome, acute myelogenous leukemia, acute lymphocytic leukemia, and multiple myeloma, uterine cervical cancer, stomach cancer, breast cancer, prostate cancer, ovary cancer, lung cancer, and colon cancer. Additionally, the drug of the present invention can be applied to humans and animals other than humans.

Also, according to the present invention, it is possible to combine a component selected from the group consisting of the compounds of the present invention or salts thereof, which are the active ingredient of the aforementioned anti-tumor effect potentiator, with a microtubule-targeting agent to prepare an anticancer agent formulated with an anti-tumor effect potentiator. In this case, the anticancer agent can be applied in the form of a mixed formulation containing the total active ingredient consisting of the microtubule-targeting agent and a component selected from the group consisting of the compounds of the present invention or salts thereof in a single preparation, alternatively, the anticancer agent can be prepared in the form of a separate preparation each individually containing these active ingredients, alternatively, the anticancer agent can be prepared as a kit formulation.

When the compound of the present invention or a salt thereof is used as a drug, a pharmaceutical carrier can be blended as needed to prepare a pharmaceutical composition. Various dosage forms can be adopted according to purpose of prevention or treatment. As the dosage form, for example, any of an oral agent, an injection, a suppository, an ointment, and a patch is possible. The compound of the present invention or a salt thereof has excellent oral absorbability and exhibits an excellent anti-tumor activity through oral administration. In light of the above, an oral agent is preferably adopted. These dosage forms can be each produced by drug preparation methods which are publicly known and commonly used by those skilled in the art.

As the pharmaceutical carrier, various kinds of organic or inorganic carrier substances commonly used as pharmaceutical materials are used, and the pharmaceutical carrier is blended in a solid preparation as for example an excipient, a binder, a disintegrant, a lubricant, and a colorant, or in a liquid preparation as for example a solvent, a solubilizing aid, a suspending agent, an isotonizing agent, a buffer, and a soothing agent. Also, an additive for drug preparation such as a preservative, an antioxidant, a colorant, a sweetener, and a stabilizing agent can also be used as needed.

When an oral solid preparation is prepared, an excipient, and if necessary, for example, an excipient, a binder, a disintegrant, a lubricant, a colorant, and a corrigent are added to the compound of the present invention, and then, for example, a tablet, a coated tablet, a granule, a powder, and a capsule can be produced by a routine procedure. When an injection is prepared, for example, a pH adjusting agent, a buffer, a stabilizer, an isotonizing agent, and a local anesthetic are added to the compound of the present invention, and a subcutaneous, intramuscular, and intravenous injection can be produced by a routine procedure.

The amount of the compound of the present invention to be incorporated in each of the aforementioned dosage unit forms is not constant but depends on, for example, the symptoms of the patient to whom the compound is applied, and on the dosage form of the compound. However, generally, the amount per dosage unit form is desirably 0.05 to 1000 mg for an oral agent, desirably 0.01 to 500 mg for an injection, and desirably 1 to 1000 mg for a suppository.

Also, the daily dose of a drug having the aforementioned dosage form varies depending on, for example, the symptoms, body weight, age, or sex of a patient, and thus cannot be generally determined. However, the daily dose of the compound of the present invention for a normal adult (weighing 50 kg) may be 0.05 to 5000 mg, preferably 0.1 to 1000 mg, and the drug is preferably administered once a day or approximately twice or three times a day in divided doses.

EXAMPLES

Hereinafter, the present invention is specifically described by Examples and Test Examples. However, the present invention is not limited to these Examples.

For various reagents used in Examples, commercial products were used unless otherwise noted. For silica gel column chromatography, Purif-Pack® SI manufactured by Schott Moritex Corporation, KP-Sil® silica prepacked column manufactured by Biotage, or HP-Sil® silica prepacked column manufactured by Biotage was used. For basic silica gel column chromatography, Purif-Pack® NH manufactured by Schott Moritex Corporation or KP-NH® prepacked column manufactured by Biotage was used. For preparative thin-layer chromatography, Kieselgel TM60F254, Art. 5744 manufactured by Merck or NH2 silica gel 60F254 plate manufactured by Wako Pure Chemical Industries, Ltd. was used. NMR spectra were measured with AL400 (400 MHz; JEOL, Ltd.), the Mercury 400 (400 MHz; Agilent Technologies, Inc.) type spectrometer, or the Inova 400 (400 MHz; Agilent Technologies, Inc.) type spectrometer equipped with the OMNMR probe (Protasis) by using, as the internal standard, tetramethylsilane when it was contained in a deuterated solvent, or by using, as the internal standard, a NMR solvent in any other case, and all the δ values were expressed as ppm. The microwave reactions were carried out using Initiator 8 manufactured by Biotage.

Also, for LCMS spectra, ACQUITY SQD (quadrupole) manufactured by Waters Corporation was used.

The abbreviations have the following meaning.

s: Singlet
d: Doublet
t: Triplet
dd: Double doublet
m: Multiplet
br: Broad
brs: Broad singlet
DMSO-$d_6$: Deuterated dimethyl sulfoxide
$CDCl_3$: Deuterated chloroform
$CD_3OD$: Deuterated methanol
Xantphos: 4,5-Bis(diphenylphosphino)-9,9-dimethylxanthene
$Pd_2(dba)_3$: Tris(dibenzylideneacetone)dipalladium (0)
$K_3PO_4$: Tripotassium phosphate MsOH: Mesylic acid
AIBN: Azobisisobutyronitrile
HPMC: Hydroxypropylmethylcellulose Example 1

Synthesis of 1-(2,3-dichlorobenzoyl)-4-((5-fluoro-6-(5-methyl-1H-pyrazol-3-ylamino)pyridin-2-yl)methyl)piperidine-4-carboxylic acid (Compound 1)

(Step a) Synthesis of tert-butyl 4-((6-bromo-5-fluoropyridin-2-yl)methyl)-4-cyanopiperidine-1-carboxylate N-Boc-4-cyanopiperidine (5.35 g, 25.4 mmol) was dissolved in 100 mL of tetrahydrofuran. After cooling the resulting mixture to −78° C., a solution of lithium diisopropylamide/tetrahydrofuran complex in cyclohexane (1.5 M, 16.5 mL, 24.8 mmol) was added while keeping the internal temperature at or below −70° C. The resulting reaction mixture was stirred at −78° C. for 20 minutes. To the reaction mixture thus obtained, 10 mL of a solution of 2-bromo-6-(bromomethyl)-3-fluoropyridine in THF (6.28 g, 23.4 mmol) was added while keeping the internal temperature at or below −70° C., followed by stirring at −78° C. for 20 minutes. To this reaction solution, a mixture of hydrochloric acid (5M, 4.95 mL, 24.8 mmol) and 95 mL of a saturated aqueous solution of ammonium chloride was added, followed by stirring at room temperature and then extraction with ethyl acetate. The extract thus obtained was washed with saturated brine and dried over anhydrous sodium sulfate, and then filtered and concentrated. The tarry residue was dissolved in 6 mL of ethyl acetate, and 50 mL of heptane was added dropwise while stirring. Seed crystals were then added, followed by stirring at room temperature for one hour. To the resulting light yellow suspension, 50 mL of heptane was further added dropwise, followed by stirring overnight. The solid thus obtained was collected by filtration and washed with a solution of ethyl acetate in heptane, and then dried under reduced pressure, whereby the titled product was obtained as an off-white solid (7.10 g, 17.8 mmol) (yield 76%). The physical property values are shown below.

$^1$H-NMR (CDCl$_3$) δ: 7.45 (1H, t, J=8.1 Hz), 7.31 (1H, dd, J=8.1, 3.5 Hz), 4.16 (2H, br), 3.09-2.93 (2H, m), 3.04 (2H, s), 1.95-1.84 (2H, m), 1.68-1.57 (2H, m), 1.48 (9H, s); ESI-MS m/z 298, 300 (MH+).

(Step b) Synthesis of tert-butyl 4-((6-(1-tert-butyl-3-methyl-1H-pyrazol-5-ylamino)-5-fluoropyridin-2-yl)methyl)-4-cyanopiperidine-1-carboxylate The compound (6.37 g, 16.0 mmol) obtained by the aforementioned step a, 5-amino-1-t-butyl-3-methylpyrazole (2.42 g, 15.8 mmol), xantphos (65.9 mg, 114 μmol), Pd$_2$(dba)$_3$ (51.1 mg, 55.8 μmol), and K$_3$PO$_4$ (3.63 g, 17.1 mmol) were placed in a reaction container, and 50 mL of toluene was added at last, followed by deaeration and argon substitution. The mixture thus obtained was stirred at 110° C. for eight hours, followed by addition of 200 mL of ethyl acetate at room temperature. The mixture thus obtained was washed with water and saturated brine and dried over sodium sulfate, and then filtered and concentrated. The residue was dissolved in 10 mL of ethyl acetate, and 40 mL of heptane was added while stirring at 75° C., followed by stirring at room temperature overnight. The resulting solid was collected by filtration and washed with 15% ethyl acetate/heptane, and then dried under reduced pressure, whereby the titled compound (4.15 g, 8.81 mmol) was obtained as a white solid (yield 56%). The physical property values are shown below.

$^1$H-NMR (CDCl$_3$) δ: 7.26 (1H, dd, J=10.7, 8.0 Hz), 6.74 (1H, dd, J=8.0, 3.2 Hz), 6.23-6.15 (2H, m), 4.19-3.92 (2H, m), 3.09-2.92 (2H, m), 2.85 (2H, s), 2.26 (3H, s), 1.95-1.86 (2H, m), 1.64 (9H, s), 1.58-1.48 (2H, m), 1.46 (9H, s); ESI-MS m/z 471 (MH+).

(Step c) Synthesis of 4-((6-(1-tert-butyl-3-methyl-1H-pyrazol-5-ylamino)-5-fluoropyridin-2-yl)methyl)-piperidine-4-carbonitrile The compound (4.11 g, 8.73 mmol) obtained by the aforementioned step b was dissolved in THF (33 mL), to which MsOH (7.0 mL) was added on a water bath. The solution thus obtained was stirred at room temperature for two hours, and the resulting content was poured into 160 mL of water. The aqueous solution thus obtained was washed with 50 mL of isopropyl ether, and 21.5 mL of 5 M sodium hydroxide was added, followed by extraction with ethyl acetate. The ethyl acetate solution thus obtained was washed with saturated brine, and then dried over anhydrous sodium sulfate. After filtration, the filtrate was concentrated, whereby the titled compound (3.09 g, 8.34 mmol) was obtained (yield 96%). The physical property values are shown below.

$^1$H-NMR (CDCl$_3$) δ: 7.22 (1H, dd, J=10.6, 8.0 Hz), 6.71 (1H, dd, J=8.0, 3.2 Hz), 6.25-6.16 (2H, m), 3.02-2.95 (2H, m), 2.91-2.84 (2H, m), 2.83 (2H, s), 2.21 (3H, s), 1.90-1.83 (2H, m), 1.61 (9H, s), 1.59-1.49 (2H, m); ESI-MS m/z 371 (MH+).

(Step d) Synthesis of 4-((6-(1-tert-butyl-3-methyl-1H-pyrazol-5-ylamino)-5-fluoropyridin-2-yl)methyl)-1-(2,3-dichlorobenzoyl)piperidine-4-carbonitrile To a mixture of the compound (3.65 g, 9.85 mmol) obtained by the aforementioned step c, 2,3-dichlorobenzoic acid (2.05 g, 10.8 mmol), and 1-hydroxybenzotriazole monohydrate (1.80 g, 13.3 mmol), 25 mL of acetonitrile was added, and then WSC hydrochloride (2.05 g, 10.7 mmol) was added. The resulting reaction mixture was stirred at room temperature overnight. Then, 30 mL of 1 M sodium hydroxide was added, followed by stirring for 15 minutes. The mixture thus obtained was extracted with ethyl acetate. The resulting ethyl acetate layer was washed sequentially with water, 1 M hydrochloric acid, water, and saturated brine. The ethyl acetate solution thus obtained was washed with anhydrous sodium sulfate, and then filtered and concentrated, whereby the titled compound (5.55 g) was obtained as a white solid (yield 100%). The physical property values are shown below.

ESI-MS m/z 543, 545 (MH+).

(Step e) Synthesis of Compound 1

The compound (524 mg, 0.964 mmol) obtained by the aforementioned step d was dissolved in 3 mL of 1,4-dioxane, and 3 mL of 5 M hydrochloric acid was then added. The resulting solution was heated at 150° C. for 10 minutes in a microwave reaction apparatus. The resulting reaction mixture was concentrated under reduced pressure, and the residue thus obtained was dissolved in chloroform, followed by washing with saturated brine. The chloroform solution thus obtained was dried over anhydrous sodium sulfate, filtered, and then concentrated under reduced pressure. The resulting residue was purified by silica gel column chromatography (chloroform/methanol=100/0 to 90/10), and the solid thus obtained was reprecipitated in ethanol-ethyl acetate, whereby the titled compound (290 mg, 0.573 mmol) was obtained as a white solid (yield 59%). The physical property values are shown in Table 9.

Examples 2 to 13

Using the raw materials listed in Tables 1 to 3, compounds of Examples 2 to 13 were synthesized according to the method of Example 1. The physical property values are shown in Tables 9 to 17.

TABLE 1

| Example | Compound name | Raw material 1 | Raw material 2 | Raw material 3 |
|---|---|---|---|---|
| 1 | 1-(2,3-dichlorobenzoyl)-4-((5-fluoro-6-(5-methyl-1H-pyrazol-3-ylamino)pyridin-2-yl)methyl)piperidine-4-carboxylic acid (compound 1) | | | |
| 2 | 1-(2-fluoro-3-trifluoromethylbenzoyl)-4-((5-fluoro-6-(5-methyl-1H-pyrazol-3-ylamino)pyridin-2-yl)methyl)piperidine-4-carboxylic acid (compound 2) | | | |
| 3 | 1-(3-chlorobenzoyl)-4-((5-fluoro-6-(5-methyl-1H-pyrazol-3-ylamino)pyridin-2-yl)methyl)piperidine-4-carboxylic acid (compound 3) | | | |
| 4 | 1-(2,3-difluorobenzoyl)-4-((5-fluoro-6-(5-methyl-1H-pyrazol-3-ylamino)pyridin-2-yl)methyl)piperidine-4-carboxylic acid (compound 4) | | | |
| 5 | 1-(2-fluoro-3-methoxybenzoyl)-4-((5-fluoro-6-(5-methyl-1H-pyrazol-3-ylamino)pyridin-2-yl)methyl)piperidine-4-carboxylic acid (compound 5) | | | |
| 6 | 1-(2-chlorobenzoyl)-4-((5-fluoro-6-(5-methyl-1H-pyrazol-3-ylamino)pyridin-2-yl)methyl)piperidine-4-carboxylic acid (compound 6) | | | |

TABLE 2

| Example | Compound name | Raw material 1 | Raw material 2 | Raw material 3 |
|---|---|---|---|---|
| 7 | 1-(2-chloro-3-methylbenzoyl)-4-((5-fluoro-6-(5-methyl-1H-pyrazol-3-ylamino)pyridin-2-yl)methyl)piperidine-4-carboxylic acid (compound 7) | 6-(bromomethyl)-2-bromo-3-fluoropyridine | 1-tert-butyl-3-methyl-1H-pyrazol-5-amine | 2-chloro-3-methylbenzoic acid |
| 8 | 1-(2-chloro-3-fluorobenzoyl)-4-((5-fluoro-6-(5-methyl-1H-pyrazol-3-ylamino)pyridin-2-yl)methyl)piperidine-4-carboxylic acid (compound 8) | 6-(bromomethyl)-2-bromo-3-fluoropyridine | 1-tert-butyl-3-methyl-1H-pyrazol-5-amine | 2-chloro-3-fluorobenzoic acid |
| 9 | 1-(2,6-dichlorobenzoyl)-4-((5-fluoro-6-(5-methyl-1H-pyrazol-3-ylamino)pyridin-2-yl)methyl)piperidine-4-carboxylic acid (compound 9) | 6-(bromomethyl)-2-bromo-3-fluoropyridine | 1-tert-butyl-3-methyl-1H-pyrazol-5-amine | 2,6-dichlorobenzoic acid |
| 10 | 1-(3-chloro-2-fluorobenzoyl)-4-((5-fluoro-6-(1H-pyrazol-3-ylamino)pyridin-2-yl)methyl)piperidine-4-carboxylic acid (compound 10) | 6-(bromomethyl)-2-bromo-3-fluoropyridine | 1-tert-butyl-1H-pyrazol-5-amine | 3-chloro-2-fluorobenzoic acid |
| 11 | 1-(3-chloro-2-fluorobenzoyl)-4-((5-methoxy-6-(5-methyl-1H-pyrazol-3-ylamino)pyridin-2-yl)methyl)piperidine-4-carboxylic acid (compound 11) | 6-(bromomethyl)-2-bromo-3-methoxypyridine | 1-tert-butyl-3-methyl-1H-pyrazol-5-amine | 3-chloro-2-fluorobenzoic acid |

TABLE 3

| Example | Compound name | Raw material 1 | Raw material 2 | Raw material 3 |
|---|---|---|---|---|
| 12 | 1-(3-chloro-2-fluorobenzoyl)-4-((5-chloro-6-(5-methyl-1H-pyrazol-3-ylamino)pyridin-2-yl)methyl)piperidine-4-carboxylic acid (compound 12) | 6-(bromomethyl)-2,3-dichloropyridine | 1-tert-butyl-3-methyl-1H-pyrazol-5-amine | 3-chloro-2-fluorobenzoic acid |

TABLE 3-continued

| Example | Compound name | Raw material 1 | Raw material 2 | Raw material 3 |
|---|---|---|---|---|
| 13 | 1-(3-chloro-2-fluorobenzoyl)-4-((5-fluoro-6-(5-methyl-1H-pyrazol-3-ylamino)pyridin-2-yl)methyl)piperidine-4-carboxylic acid (compound 13) | (structure) | (structure) | (structure) |

Example 14

Synthesis of 1-(3-chloro-2-fluorobenzoyl)-4-((5-fluoro-6-(5-methyl-1H-pyrazol-3-ylamino)pyridin-2-yl)methyl)-N-methylpiperidine-4-carboxamide (Compound 14)

To a mixture of the compound 13 (50 mg, 0.1 mmol) obtained in Example 13, 1-ethyl-3-(3-dimethylaminopropyl)carbodiimide hydrochloride (40 mg, 0.21 mmol), 1-hydroxybenzotriazole monohydrate (30 mg, 0.22 mmol), methylamine hydrochloride (25 mg, 0.37 mmol), and 1 mL of dimethylformamide, 0.05 mL of triethylamine was added, followed by stirring at room temperature for 13 hours. To the resulting reaction mixture, water was added, followed by extraction with ethyl acetate. The resulting extract was dried over anhydrous magnesium sulfate, filtered, and then concentrated. The residue thus obtained was purified by HPLC, whereby the titled compound (41 mg, 0.082 mmol) was obtained as a white solid (yield 82%). The physical property values are shown in Tables 9 to 17.

Examples 15 to 21

In Examples 15 to 21, using the raw materials specified in Tables 4 to 5, compounds were synthesized by a method according to Example 14. The physical property values are shown in Tables 9 to 17.

TABLE 4

| Example | Compound name | Raw material 4 |
|---|---|---|
| 14 | 1-(3-chloro-2-fluorobenzoyl)-4-((5-fluoro-6-(5-methyl-1H-pyrazol-3-ylamino)pyridin-2-yl)methyl)-N-methylpiperidine-4-carboxyamide (compound 14) | Methylamine hydrochloride |
| 15 | 1-(3-chloro-2-fluorobenzoyl)-4-((5-fluoro-6-(5-methyl-1H-pyrazol-3-ylamino)pyridin-2-yl)methyl)piperidine-4-carboxyamide (compound 15) | Ammonium chloride |
| 16 | 1-(3-chloro-2-fluorobenzoyl)-4-((5-fluoro-6-(5-methyl-1H-pyrazol-3-ylamino)pyridin-2-yl)methyl)-N,N-dimethylpiperidine-4-carboxyamide (compound 16) | Dimethylamine |
| 17 | 1-(3-chloro-2-fluorobenzoyl)-N-cyclopropyl-4-((5-fluoro-6-(5-methyl-1H-pyrazol-3-ylamino)pyridin-2-yl)methyl)piperidine-4-carboxyamide (compound 17) | Cyclopropylamine |
| 18 | 1-(3-chloro-2-fluorobenzoyl)-N-cyclobutyl-4-((5-fluoro-6-(5-methyl-1H-pyrazol-3-ylamino)pyridin-2-yl)methyl)piperidine-4-carboxyamide (compound 18) | Cyclobutylamine |
| 19 | azetidin-1-yl(1-(3-chloro-2-fluorobenzoyl)-4-((5-fluoro-6-(5-methyl-1H-pyrazol-3-ylamino)pyridin-2-yl)methyl)piperidin-4-yl)methanone (compound 19) | Azetidine hydrochloride |

TABLE 5

| Example | Compound name | Raw material 4 |
|---|---|---|
| 20 | (1-(3-chloro-2-fluorobenzoyl)-4-((5-fluoro-6-(5-methyl-1H-pyrazol-3-ylamino)pyridin-2-yl)methyl)piperidin-4-yl)(pyrrolidin-1-yl)methanone (compound 20) | Pyrrolidine |
| 21 | (1-(3-chloro-2-fluorobenzoyl)-4-((5-fluoro-6-(5-methyl-1H-pyrazol-3-ylamino)pyridin-2-yl)methyl)piperidin-4-yl)(isoxazolidin-2-yl)methanone (compound 21) | Isoxazolidine hydrochloride |

Example 22

Synthesis of (3-chloro-2-fluorophenyl)(4-((5-fluoro-6-(5-methyl-1H-pyrazol-3-ylamino)pyridin-2-yl)methyl)-4-(5-methyl-1,2,4-oxadiazol-3-yl)piperidin-1-yl)methanone (Compound 22)

(Step a) Synthesis of tert-butyl 4-((6-(1-tert-butyl-3-methyl-1H-pyrazol-5-ylamino)-5-fluoropyridin-2-yl)methyl)-4-(N'-hydroxycarbamimidoyl)piperidine-1-carboxylate The compound (50 g) obtained in Example 1 (Step b) was dissolved in 530 mL of ethanol at 60° C. The resulting solution was returned to room temperature and 65 mL of a 50% aqueous solution of hydroxylamine was added, followed by stirring at 60° C. for 46 hours. The resulting reaction solution was added to distilled water, followed by extraction with ethyl acetate. The resulting organic layer was washed with distilled water and saturated brine. The resulting solution was dried over sodium sulfate and then concentrated under reduced pressure, whereby the titled compound (53 g, 106 mmol) was obtained (yield 100%). The physical property values are shown below.

ESI-MS m/z 504 (MH+).

(Step b) Synthesis of tert-butyl4-((6-(1-tert-butyl-3-methyl-1H-pyrazol-5-ylamino)-5-fluoropyridin-2-yl)methyl)-4-(5-methyl-1,2,4-oxadiazol-3-yl)piperidine-1-carboxylate The compound (53 g, 106 mmol) obtained by the aforementioned step a was suspended in 525 mL of toluene, and 10 mL of acetic anhydride was added, followed by stirring at room temperature for one hour and 20 minutes, and then at 100° C. for 16 hours. To the resulting reaction solution, 175 mL of aqueous ammonia, 500 mL of distilled water, and 500 mL of ethyl acetate were sequentially added in an ice bath, followed by washing with saturated brine. The resulting aqueous layer was extracted with ethyl acetate, and the resulting organic layer was washed with saturated brine and dried over sodium sulfate, and then concentrated under reduced pressure, whereby the titled compound (58 g) was obtained as a crude purified product. The physical property values are shown below.

ESI-MS m/z 528 (MH+).

(Step c) Synthesis of N-(1-tert-butyl-3-methyl-1H-pyrazol-5-yl)-3-fluoro-6-((4-(5-methyl-1,2,4-oxadiazol-3-yl)piperidin-4-yl)methyl)pyridine-2-amine The compound (57 g) obtained by the aforementioned step b was dissolved in 210 mL of acetonitrile, and 27 mL of mesylic acid was added on an ice bath, followed by stirring in an ice bath for one hour, and then at room temperature for 17 hours. The resulting reaction solution was added to 500 mL of distilled water in an ice bath, followed by washing with 500 mL of diisopropyl ether. To the resulting aqueous layer, 100 mL of 5 M sodium hydroxide was added in an ice bath, and the aqueous layer was extracted with ethyl acetate. The resulting organic layer was washed with saturated brine and dried over sodium sulfate, and then concentrated under reduced pressure, whereby the titled compound (44 g, 102 mmol) was obtained (yield 91%). The physical property values are shown below.

ESI-MS m/z 428 (MH+).

(Step d) Synthesis of 4-((6-(1-tert-butyl-3-methyl-1H-pyrazol-5-ylamino)-5-fluoropyridin-2-yl)methyl)-4-(5-methyl-1,2,4-oxadiazol-3-yl)piperidin-1-yl)(3-chloro-2-fluorophenyl)methanone The compound (44 g) obtained by the aforementioned step c, 3-chloro-2-fluorobenzoic acid (20 g), and 1-hydroxybenzotriazole monohydrate (21 g) were dissolved in 343 mL of acetonitrile, and in an ice bath, 1-ethyl-3-(3-dimethylaminopropyl)carbodiimide hydrochloride (22 g) was added, followed by stirring at room temperature for 15 hours. To the resulting reaction solution, 1 M sodium hydroxide (500 mL) was added, followed by extraction with ethyl acetate. The resulting organic layer was washed with distilled water, 1 M hydrochloric acid, distilled water, and saturated brine, and then dried over sodium sulfate and concentrated under reduced pressure. The resulting residue was crystallized from heptane-ethyl acetate, whereby the titled compound (52 g, 89 mmol) was obtained (yield 86%). The physical property values are shown below.

ESI-MS m/z 584,586 (MH+).

(Step e) Synthesis of Compound 22

The compound (2.94 g, 5.03 mmol) obtained by the aforementioned step d was dissolved in 30 mL of 5 M hydrochloric acid and 20 mL of 2-propanol, followed by heating at 100° C. for two hours. The resulting reaction solution was cooled on ice, and water and 5 M sodium hydroxide were then added to adjust pH to approximately 8, followed by extraction with ethyl acetate. The extract thus obtained was washed with water and saturated brine, and then dried over sodium sulfate and concentrated under reduced pressure. The resulting residue was purified by silica gel column chromatography (chloroform/methanol=100/0 to 95/5), whereby the titled compound (2.26 g, 4.28 mmol) was obtained (yield 85%). The physical property values are shown in Tables 9 to 17.

Examples 23 to 27

In Examples 23 to 27, using the raw materials specified in Tables 6 to 7, compounds were synthesized by a method according to Example 22. The physical property values are shown in Tables 9 to 17.

TABLE 6

| Example | Compound name | Raw material 5 | Raw material 6 | Raw material 7 |
|---|---|---|---|---|
| 22 | (3-chloro-2-fluorophenyl)(4-((5-fluoro-6-(5-methyl-1H-pyrazol-3-ylamino)pyridin-2-yl)methyl)-4-(5-methyl-1,2,4-oxadiazol-3-yl)piperidin-1-yl)methanone (compound 22) | | | Acetic anhydride |

TABLE 6-continued

| Example | Compound name | Raw material 5 | Raw material 6 | Raw material 7 |
|---------|---------------|----------------|----------------|----------------|
| 23 | (2,3-dichlorophenyl)(4-((5-fluoro-6-(5-methyl-1H-pyrazol-3-ylamino)pyridin-2-yl)methyl)-4-(5-methyl-1,2,4-oxadiazol-3-yl)piperidin-1-yl)methanone (compound 23) | 6-(bromomethyl)-2-bromo-3-fluoropyridine | 2,3-dichlorobenzoic acid | Acetic anhydride |
| 24 | (3-chloro-2-fluorophenyl)(4-((5-fluoro-6-(5-methyl-1H-pyrazol-3-ylamino)pyridin-2-yl)methyl)-4-(1,2,4-oxadiazol-3-yl)piperidin-1-yl)methanone (compound 24) | 6-(bromomethyl)-2-bromo-3-fluoropyridine | 3-chloro-2-fluorobenzoic acid | Triethyl orthoformate |
| 25 | (3-chloro-2-fluorophenyl)(4-((5-fluoro-6-(5-methyl-1H-pyrazol-3-ylamino)pyridin-2-yl)methyl)-4-(5-(trifluoromethyl)-1,2,4-oxadiazol-3-yl)piperidin-1-yl)methanone (compound 25) | 6-(bromomethyl)-2-bromo-3-fluoropyridine | 3-chloro-2-fluorobenzoic acid | Trifluoroacetic anhydride |

TABLE 7

| Example | Compound name | Raw material 5 | Raw material 6 | Raw material 7 |
|---------|---------------|----------------|----------------|----------------|
| 26 | (3-chloro-2-fluorophenyl)(4-((5-methoxy-6-(5-methyl-1H-pyrazol-3-ylamino)pyridin-2-yl)methyl)-4-(5-methyl-1,2,4-oxadiazol-3-yl)piperidin-1-yl)methanone (compound 26) | 6-(bromomethyl)-2-bromo-3-methoxypyridine | 3-chloro-2-fluorobenzoic acid | Acetic anhydride |
| 27 | (3-chloro-2-fluorophenyl)(4-((5-chloro-6-(5-methyl-1H-pyrazol-3-ylamino)pyridin-2-yl)methyl)-4-(5-methyl-1,2,4-oxadiazol-3-yl)piperidin-1-yl)methanone (compound 27) | 6-(bromomethyl)-2,3-dichloropyridine | 3-chloro-2-fluorobenzoic acid | Acetic anhydride |

Example 28

Synthesis of (3-chloro-2-fluorophenyl)(4-((5-fluoro-6-(5-methyl-1H-pyrazol-3-ylamino)pyridin-2-yl)methyl)-4-(5-methyl-1,3,4-oxadiazol-3-yl)piperidin-1-yl)methanone (Compound 28)

(Step a) Synthesis of tert-butyl 2-(1-(3-chloro-2-fluorobenzoyl)-4-((5-fluoro-6-(5-methyl-1H-pyrazol-3-ylamino)pyridin-2-yl)methyl)piperidin-4-carbonyl)hydrazine carboxylate The compound 13 (62 mg, 0.13 mmol) obtained in Example 13, tert-butoxycarbonyl hydrazide (25 mg, 0.19 mmol), and 1-hydroxybenzotriazole monohydrate (30 mg, 0.22 mmol) were dissolved in 3 mL of dimethylformamide, and (1-ethyl-3-(3-dimethylaminopropyl)carbodiimide hydrochloride (41 mg, 0.22 mmol) was added, followed by stirring at room temperature for three hours. To the resulting reaction mixture, water was added, and the resulting mixture was extracted with ethyl acetate and then dried over anhydrous magnesium sulfate. The resulting mixture was filtered and concentrated, and the residue thus obtained was purified by silica gel column chromatography (chloroform/methanol=100/0 to 95/5), whereby the titled compound (70 mg, 0.12 mmol) was obtained (yield 92%). The physical property values are shown below.

ESI-MS m/z 604, 606 (MH+).

(Step b) Synthesis of Compound 28

The compound (70 mg, 0.12 mmol) obtained by the aforementioned step a was dissolved in 4 mL of chloroform, and 2 mL of trifluoroacetic acid was added, followed by stirring at room temperature for three hours. The resulting reaction mixture was concentrated, and to the residue, chloroform and a saturated aqueous solution of sodium bicarbonate were added for phase separation. The chloroform layer was dried over anhydrous magnesium sulfate, filtered, and concentrated. To the residue thus obtained, 4 mL of toluene and 0.5 mL of ortho ethyl acetate were added, followed by stirring while heating at 110° C. for two hours. To the resulting reaction solution, water was added at room temperature, followed by extraction with ethyl acetate. The extract thus obtained was dried over anhydrous magnesium sulfate, and then filtered and concentrated. The residue thus obtained was purified by silica gel column chromatography (chloroform/methanol=100/0 to 90/10), whereby the titled compound (39 mg, 0.077 mmol) was obtained (yield 64%). The physical property values are shown in Tables 9 to 17.

Example 29

Synthesis of (3-chloro-2-fluorophenyl)(4-((5-fluoro-6-(5-methyl-1H-pyrazol-3-ylamino)pyridin-2-yl)methyl)-4-(3-methyl-1,2,4-oxadiazol-5-yl)piperidin-1-yl)methanone (Compound 29)

To a mixture of the compound 13 (49 mg, 0.10 mmol) obtained in Example 13, 1-ethyl-3-(3-dimethylaminopropyl)carbodiimide hydrochloride (38 mg, 0.20 mmol), 1-hydroxybenzotriazole monohydrate (27 mg, 0.20 mmol), acetamidoxime (15 mg, 0.20 mmol), and dimethylformamide (1 mL), diisopropylethylamine (0.07 mL) was added, followed by stirring at room temperature for seven hours. To the resulting reaction mixture, water was added, followed by extraction with ethyl acetate. The extract thus obtained was dried over anhydrous sodium sulfate, and then filtered and concentrated. To the crude product thus obtained, 1,4-dioxane (1 mL) was added, and the resulting mixture was irradiated at 120° C. for six hours while stirring using a microwave reaction apparatus (Biotage Initiator 8). After concentration, the residue thus obtained was purified by HPLC, whereby the titled compound (29 mg, 0.055 mmol) was obtained as a light orange solid (yield 55%). The physical property values are shown in Tables 9 to 17.

Comparative Example 1

Synthesis of 5-(1-(3-chloro-2-fluorobenzoyl)-4-((6-(1H-pyrazol-3-ylamino)pyridin-2-yl)methyl)piperidin-4-yl)-1,3,4-oxadiazol-2(3H)-one (Comparative Compound 1)

Comparative Compound 1 was synthesized as follows in accordance with the method described in International Publication No. WO2009/104802. To 5-(4-((6-((1-tert-butyl-1H-pyrazol-5-yl)amino)pyridin-2-yl)methyl)-1-(3-chloro-2-fluorobenzoyl)piperidin-4-yl)-1,3,4-oxadiazol-2-(3H)-one (4.45 g, 8.03 mmol), 5 M hydrochloric acid (40 mL) and 2-propanol (40 mL) were added, followed by stirring at 100° C. for four hours. To the resulting reaction mixture, 5 M sodium hydroxide (40 mL) was added, and the resulting solution was separated and extracted with chloroform. The resulting chloroform extract was dried over anhydrous magnesium sulfate, and then filtered and concentrated. The residue thus obtained was purified by silica gel column chromatography (chloroform/methanol=100/0 to 95/5), and then washed in ethyl acetate while stirring, whereby the titled compound (1.63 g, 3.29 mmol) was obtained as a light orange solid (yield 41%). The physical property values are shown in Table 18.

Comparative Examples 2 to 5 and 7

In Comparative Examples 2 to 5 and 7, using the raw materials specified in Table 8, compounds were synthesized according to a method equivalent to that used in Example 1. The physical property values are shown in Table 18.

TABLE 8

| Comparative Example | Compound name | Raw material 8 | Raw material 9 | Raw material 10 |
|---|---|---|---|---|
| 2 | 1-(3-chloro-2-fluorobenzoyl)-4-((4-cyclopropyl-6-(thiazol-2-ylamino)pyridin-2-yl)methyl)piperidine-4-carboxylic acid (Comparative Compound 2) | [structure: 2-chloro-6-(bromomethyl)-4-cyclopropylpyridine] | [structure: 2-aminothiazole] | [structure: 3-chloro-2-fluorobenzoic acid] |
| 3 | 1-(3-chloro-2-fluorobenzoyl)-4-((4-cyclopropyl-6-(5-methyl-1H-pyrazol-3-ylamino)pyridin-2-yl)methyl)piperidine-4-carboxylic acid (Comparative Compound 3) | [structure: 2-chloro-6-(bromomethyl)-4-cyclopropylpyridine] | [structure: 1-tert-butyl-3-methyl-1H-pyrazol-5-amine] | [structure: 3-chloro-2-fluorobenzoic acid] |
| 4 | 1-(3-chloro-2-fluorobenzoyl)-4-((3-methoxy-6-(thiazol-2-ylamino)pyridin-2-yl)methyl)piperidine-4-carboxylic acid (Comparative Compound 4) | [structure: 6-bromo-2-(bromomethyl)-3-methoxypyridine] | [structure: 2-aminothiazole] | [structure: 3-chloro-2-fluorobenzoic acid] |
| 5 | 4-((6-(1H-pyrazol-3-ylamino)pyridin-2-yl)methyl)-1-(3-chloro-2-fluorobenzoyl)piperidine-4-carboxylic acid (Comparative Compound 5) | [structure: 2,6-dibromo-methylpyridine] | [structure: 1-tert-butyl-1H-pyrazol-5-amine] | [structure: 3-chloro-2-fluorobenzoic acid] |
| 7 | 1-(3-chloro-2-fluorobenzoyl)-4-((3-fluoro-6-(5-methyl-1H-pyrazol-3-ylamino)pyridin-2-yl)methyl)piperidine-4-carboxylic acid (Comparative Compound 7) | [structure: 2-chloro-6-(bromomethyl)-3-fluoropyridine] | [structure: 1-tert-butyl-3-methyl-1H-pyrazol-5-amine] | [structure: 3-chloro-2-fluorobenzoic acid] |

Comparative Example 6

Synthesis of 1-(3-chloro-2-fluorobenzoyl)-4-((5-cyano-6-(5-methyl-1H-pyrazol-3-ylamino)pyridin-2-yl)methyl)piperidine-4-carboxylic acid (Comparative Compound 6)

(Step a) Synthesis of tert-butyl 4-ethyl 4-((5-bromo-6-chloropyridin-2-yl)methyl)piperidine-1,4-dicarboxylate In 21 mL of carbon tetrachloride, 3-bromo-2-chloro-6-methylpyridine (880 mg, 4.26 mmol) was dissolved, and N-bromosuccinimide (682 mg, 3.83 mmol) and AIBN (70 mg, 0.426 mmol) were added, followed by stirring at 90° C. for one hour. The resulting reaction solution was concentrated, and the residue thus obtained was purified by silica gel column chromatography (chloroform/methanol=100/0 to 95/5), whereby 3-bromo-6-(bromomethyl)-2-chloropyridine was obtained as a crude purified product.

In 18 mL of tetrahydrofuran, ethyl N-Boc piperidine carboxylate (1.16 mL, 4.72 mmol) was dissolved, and a solution of a lithium diisopropylamide/tetrahydrofuran complex in cyclohexane (1.5 M, 3.3 mL, 4.96 mmol) was added at −78° C., followed by stirring for 40 minutes. Then, 2 mL of the solution of 3-bromo-6-(bromomethyl)-2-chloropyridine in tetrahydrofuran obtained as above was added dropwise, followed by further stirring for 10 minutes. To the resulting reaction solution, a saturated aqueous solution of ammonium chloride was added and the temperature was raised, and the solution was partitioned between water and ethyl acetate. The resulting ethyl acetate layer was washed with saturated brine and dried over anhydrous magnesium sulfate, and then filtered and concentrated. The residue thus obtained was purified by silica gel column chromatography (hexane/ethyl acetate=95/5 to 65/35), whereby the titled compound (592 mg, 1.28 mmol) was obtained (yield 27%). The physical property values are shown below.

ESI-MS m/z 461, 463, 465 (MH+).

(Step b) Synthesis of ethyl 4-((5-bromo-6-chloro-pyridin-2-yl)methyl)-1-(3-chloro-2-fluorobenzoyl)piperidine-4-carboxylate The compound (590 mg, 1.28 mmol) obtained by the aforementioned step a was dissolved in 5 mL of chloroform, and 2 mL of trifluoroacetic acid was added, followed by stirring at room temperature for one hour. The resulting reaction solution was concentrated and dissolved in 5 mL of DMF. Then, 1H-benzo[b][1,2,3]-triazol-1-yl 3-chloro-2-fluorobenzoate (411 mg, 1.41 mmol) and N,N-diisopropyl-ethylamine (0.45 mL, 2.56 mmol) was added at 0° C., followed by stirring for 15 minutes. Water was added, and the resulting mixture was extracted with ethyl acetate. The resulting ethyl acetate layer was washed with water and saturated brine, and dried over anhydrous magnesium sulfate, and then filtered and concentrated. The residue thus obtained was purified by silica gel column chromatography (hexane/ethyl acetate=90/10 to 50/50), whereby the titled compound (581 mg, 1.13 mmol) was obtained (yield 88%). The physical property values are shown below.

ESI-MS m/z 517, 519, 521 (MH+).

(Step c) Synthesis of 4-((5-bromo-6-chloropyridin-2-yl)methyl)-1-(3-chloro-2-fluorobenzoyl)piperidine-4-carboxylic acid The compound (310 mg, 0.598 mmol) obtained by the aforementioned step b was dissolved in 6 mL of ethanol, and 5 M sodium hydroxide (0.96 mL) was added, followed by stirring at 80° C. for 1.5 hours. The resulting reaction solution was diluted with water, and 5 M hydrochloric acid was added to adjust pH to 1, followed by extraction with ethyl acetate. The resulting ethyl acetate layer was washed with water and saturated brine, and dried over anhydrous magnesium sulfate, and then filtered and concentrated. The residue thus obtained was purified by silica gel column chromatography (hexane/ethyl acetate=30/70 to 0/100→chloroform/methanol=100/0 to 90/10), whereby the titled compound (259 mg, 0.526 mmol) was obtained (yield 88%). The physical property values are shown below.

ESI-MS m/z 489, 491, 493 (MH+).

(Step d) Synthesis of Comparative Compound 6

To the compound (80 mg, 0.163 mmol) obtained by the aforementioned step c and copper cyanide (16 mg, 0.180 mmol), 1 mL of N-methylpyrrolidone was added, and the resulting mixture was irradiated at 195° C. for 40 minutes while stirring using a microwave reaction apparatus (Biotage Initiator 8). The resulting reaction solution was diluted with water and 1 M hydrochloric acid was added, followed by extraction with ethyl acetate. The resulting ethyl acetate layer was washed with water and saturated brine, and dried over anhydrous magnesium sulfate, and then filtered and concentrated. The residue thus obtained was purified by silica gel column chromatography (hexane/ethyl acetate=50/50 to 0/100→chloroform/methanol=100/0 to 90/10), whereby 4-((5-cyano-6-chloropyridin-2-yl)methyl)-1-(3-chloro-2-fluorobenzoyl)piperidine-4-carboxylic acid (9 mg) was obtained as a crude purified product. To the crude purified product obtained in this step (9 mg), 5-amino-1-tert-butyl-3-methylpyrazole (3.5 mg, 0.022 mmol), xantphos (2.4 mg, 0.0041 mmol), Pd$_2$(dba)$_3$ (2.0 mg, 0.0023 mmol), and potassium phosphate (8.7 mg, 0.041 mmol), 0.2 mL of dioxane was added, followed by stirring at 100° C. for 3.5 hours. The resulting reaction solution was diluted with water and extracted with ethyl acetate. The resulting ethyl acetate layer was washed with water and saturated brine, and dried over anhydrous magnesium sulfate, and then filtered and concentrated. The residue thus obtained was purified by silica gel column chromatography (hexane/ethyl acetate=25/75 to 0/100→chloroform/methanol=100/0 to 90/10), whereby 4-((6-(1-tert-butyl-5-methyl-1H-pyrazol-3-ylamino)-5-cyanopyridin-2-yl)methyl)-1-yl)-1-(3-chloro-2-fluorobenzoyl)piperidine-4-carboxylic acid (4 mg) was obtained as a crude product. The crude product thus obtained (4 mg) was dissolved in 0.5 mL of trifluoroacetic acid and 0.05 mL of anisole, followed by stirring while heating at 85° C. for one hour. After concentration, the residue thus obtained was purified by reverse phase HPLC, whereby the titled compound (1 mg, 0.002 mmol) was obtained (yield 1%). The physical property values are shown in Table 18.

TABLE 9

| Example | Structural formula | Physical property value |
| --- | --- | --- |
| Example 1 | 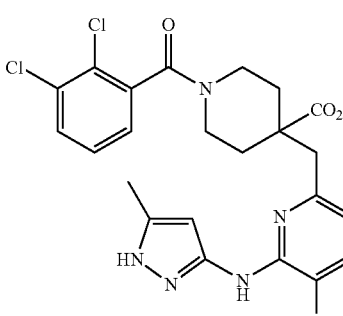 | $^1$H-NMR (DMSO-D$_6$) δ: 10.05 (1H, brs), 7.70-7.65 (1H, m), 7.59-7.54 (1H, m), 7.46-7.29 (2H, m), 6.72-6.68 (1H, m), 6.30-6.29 (1H, m), 4.23-4.18 (1H, m), 3.26-3.20 (1H, m), 3.09-2.95 (4H, m), 2.27-2.26 (3H, m), 2.05-2.00 (1H, m), 1.90-1.83 (1H, m), 1.67-1.49 (2H, m); ESI-MS m/z 506, 508 (MH+). |

TABLE 9-continued

| Example | Structural formula | Physical property value |
|---|---|---|
| Example 2 | 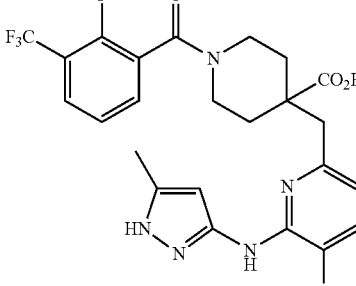 | $^1$H-NMR (DMSO-D$_6$) δ: 10.05 (1H, brs), 7.86 (1H, t, J = 7.7 Hz), 7.75 (1H, t, J = 7.7 Hz), 7.57 (1H, dd, J = 11.1, 8.2 Hz), 7.48 (1H, t, J = 7.7 Hz), 6.70 (1H, dd, J = 8.2, 2.8 Hz), 6.29 (1H, s), 4.20 (1H, d, J = 13.7 Hz), 3.36 (1H, d, J = 13.7 Hz), 3.11-2.98 (4H, m), 2.25 (3H, s), 2.02 (1H, d, J = 13.7 Hz), 1.91-1.87 (1H, m), 1.64-1.50 (2H, m); ESI-MS m/z 524 (MH+). |
| Example 3 | | $^1$H-NMR (CDCl$_3$) δ: 7.38-7.00 (5H, m), 6.70-6.58 (1H, m), 5.68 (1H, s), 4.60-4.45 (1H, m), 3.40-3.09 (4H, m), 3.04-2.89 (1H, m), 2.40-2.10 (2H, m), 2.24 (3H, s), 1.71-1.42 (2H, m); ESI-MS m/z 472, 474 (MH+). |

TABLE 10

| Example | Structural formula | Physical property value |
|---|---|---|
| Example 4 | 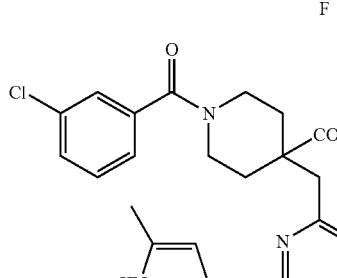 | $^1$H-NMR (CDCl$_3$) δ: 7.30-6.95 (4H, m), 6.68-6.60 (1H, m), 5.69 (1H, s), 4.64-4.55 (1H, m), 3.42-3.15 (4H, m), 3.03-2.90 (1H, m), 2.50-2.30 (1H, m), 2.28-2.16 (1H, m), 2.23 (3H, s), 1.58-1.40 (2H, m); ESI-MS m/z 474 (MH+). |
| Example 5 | | $^1$H-NMR (DMSO-D$_6$) δ: 9.23 (1H, brs), 7.73-7.65 (1H, m), 7.58-7.46 (2H, m), 7.23-7.13 (1H, m), 6.83-6.79 (1H, m), 6.60 (1H, s), 4.51-4.40 (1H, m), 4.17 (3H, s), 3.75-3.36 (1H, m), 3.52-3.30 (2H, m), 3.20 (2H, s), 2.46 (3H, s), 2.39-2.27 (1H, m), 2.23-2.12 (1H, m), 1.97-1.78 (2H, m); ESI-MS m/z 486 (MH+). |

TABLE 10-continued

| Example | Structural formula | Physical property value |
|---|---|---|
| Example 6 | 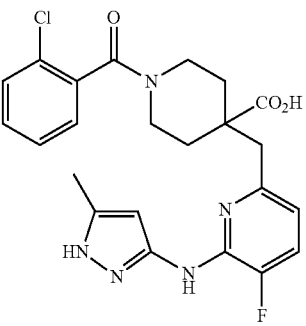 [SMILES: Cc1cc(Nc2nc(CC3(C(=O)O)CCN(C(=O)c4ccccc4Cl)CC3)ccc2F)n[nH]1] | $^1$H-NMR (CDCl$_3$) δ: 7.38-7.02 (4H, m), 6.68-6.59 (1H, m), 5.68 (1H, s), 4.66-4.56 (1H, m), 3.33-3.09 (4H, m), 3.03-2.91 (1H, m), 2.40-2.25 (1H, m), 2.24 (3H, s), 2.20-2.10 (1H, m), 1.62-1.40 (2H, m); ESI-MS m/z 472, 474 (MH+). |
| Example 7 | 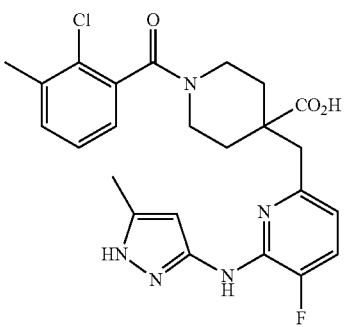 [SMILES: Cc1cc(Nc2nc(CC3(C(=O)O)CCN(C(=O)c4cccc(C)c4Cl)CC3)ccc2F)n[nH]1] | $^1$H-NMR (DMSO-D$_6$) δ: 9.24 (1H, brs), 7.75-7.43 (4H, m), 6.87-6.79 (1H, m), 6.60 (1H, s), 4.54-4.41 (1H, m), 3.71-3.29 (3H, m), 3.20 (2H, s), 2.66 (3H, s), 2.46 (3H, s), 2.39-2.28 (1H, m), 2.22-2.12 (1H, m), 2.00-1.80 (2H, m); ESI-MS m/z 486, 488 (MH+). |

TABLE 11

| Example | Structural formula | Physical property value |
|---|---|---|
| Example 8 | 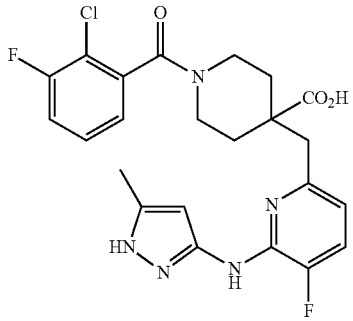 | $^1$H-NMR (DMSO-D$_6$) δ: 9.23 (1H, brs), 7.82-7.63 (3H, m), 7.60-7.48 (1H, m), 6.85-6.79 (1H, m), 6.66-6.56 (1H, m), 4.56-4.44 (1H, m), 3.72-3.29 (3H, m), 3.24-3.12 (2H, m), 2.47 (3H, s), 2.41-2.29 (1H, m), 2.24-2.12 (1H, m), 2.01-1.80 (2H, m); ESI-MS m/z 490, 492 (MH+). |
| Example 9 | 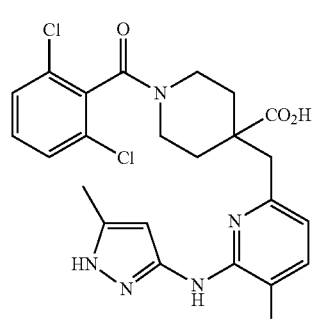 | $^1$H-NMR (DMSO-D$_6$) δ: 9.23 (1H, brs), 7.89-7.63 (4H, m), 6.85-6.79 (1H, m), 6.61 (1H, s), 4.58-4.48 (1H, m), 3.72-3.30 (3H, m), 3.26-3.14 (2H, m), 2.47 (3H, s), 2.41-2.30 (1H, m), 2.27-2.16 (1H, m), 2.01-1.85 (2H, m); ESI-MS m/z 506, 508 (MH+). |

TABLE 11-continued

| Example | Structural formula | Physical property value |
|---|---|---|
| Example 10 | 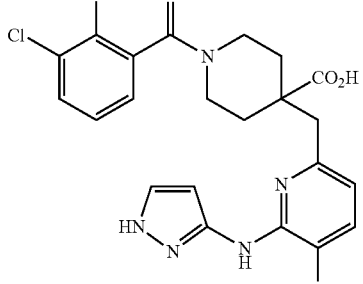 | $^1$H-NMR (DMSO-D$_6$) δ 9.07 (1H, brs), 7.65 (1H, td, J = 7.8, 2.0 Hz), 7.49 (1H, d, J = 2.0 Hz), 7.41-7.35 (2H, m), 7.29 (1H, t, J = 7.8 Hz), 6.53-6.51 (2H, m), 4.19 (1H, d, J = 13.7 Hz), 3.34 (1H, d, J = 13.7 Hz), 3.07-3.02 (2H, m), 2.90 (1H, d, J = 13.4 Hz), 2.87 (1H, d, J = 13.4 Hz), 2.03 (1H, d, J = 13.4 Hz), 1.88 (1H, d, J = 13.4 Hz), 1.61-1.48 (2H, m); ESI-MS m/z 476, 478 (MH+). |
| Example 11 | 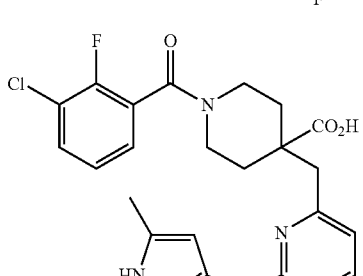 | $^1$H-NMR (DMSO-D$_6$) δ: 10.68 (1H, brs), 7.67 (1H, t, J = 7.6 Hz), 7.51 (1H, d, J = 8.0 Hz), 7.37 (1H, t, J = 6.7 Hz), 7.30 (1H, t, J = 7.6 Hz), 6.85 (1H, d, J = 8.0 Hz), 6.14 (1H, s), 4.32-4.20 (1H, m), 3.97 (3H, s), 3.43-3.32 (1H, m), 3.15-2.96 (4H, m), 2.27 (3H, s), 2.12-2.03 (1H, m), 1.99-1.87 (1H, m), 1.70-1.45 (2H, m); ESI-MS m/z 502, 504 (MH+) |

TABLE 12

| Example | Structural formula | Physical property value |
|---|---|---|
| Example 12 | 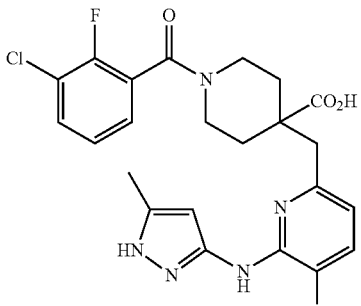 | $^1$H-NMR (CDCl$_3$) δ: 7.55 (1H, d, J = 8.7 Hz), 7.42-7.35 (1H, m), 7.34 (1H, s), 7.25-7.16 (2H, m), 6.70-6.61 (1H, m), 5.67 (1H, s), 4.61-4.53 (1H, m), 3.40-3.09 (4H, m), 3.05-2.94 (1H, m), 2.37-2.10 (2H, m), 2.25 (3H, s), 1.61-1.40 (2H, m); ESI-MS m/z 506, 508 (MH+). |
| Example 13 | 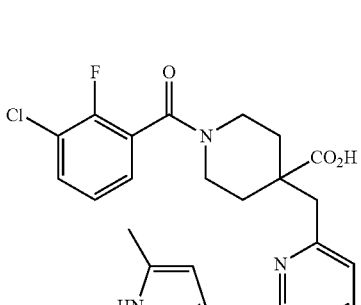 | $^1$H-NMR (DMSO-D$_6$) δ: 10.13 (1H, brs), 7.68-7.64 (1H, m), 7.58 (1H, dd, J = 11.0 Hz, 8.0 Hz), 7.38-7.35 (1H, m), 7.29 (1H, t, J = 8.0 Hz), 6.73-6.70 (1H, m), 6.29 (1H, s), 4.21-4.18 (1H, m), 3.38-3.34 (1H, m), 3.09-2.99 (4H, m), 2.27 (3H, s), 2.03-1.99 (1H, m), 1.89-1.87 (1H, m), 1.63-1.49 (2H, m); ESI-MS m/z 490, 492 (MH+). |

TABLE 12-continued

| Example | Structural formula | Physical property value |
|---|---|---|
| Example 14 | 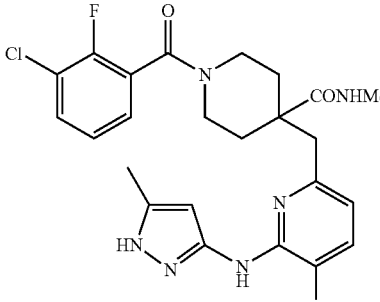 | $^1$H-NMR (DMSO-D$_6$) δ: 11.79 (1H, s), 8.68 (0.5H, s), 7.68-7.61 (2H, m), 7.36-7.27 (3H, m), 6.41 (1.5H, s), 4.06-4.01 (1H, m), 3.32 (3H, s), 3.30-3.28 (1H, m), 3.20-3.16 (1H, m), 3.09-3.03 (1H, m), 2.87-2.82 (2H, m), 2.13 (3H, s), 2.05-2.01 (1H, m), 1.91-1.87 (1H, m), 1.61-1.49 (2H, m); ESI-MS m/z 503, 505 (MH+). |

TABLE 13

| Example | Structural formula | Physical property value |
|---|---|---|
| Example 15 | 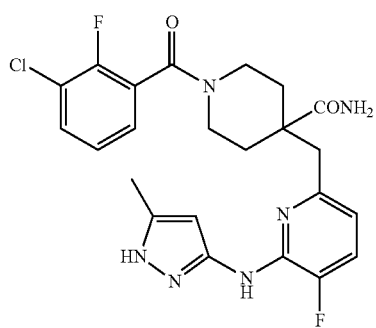 [SMILES: Cc1cc(Nc2nc(CC3(C(N)=O)CCN(C(=O)c4cccc(Cl)c4F)CC3)ccc2F)n[nH]1] | $^1$H-NMR (DMSO-D$_6$) δ: 11.79 (1H brs), 8.66 (0.5H, brs), 7.65 (1H, td, J = 7.7, 1.6 Hz), 7.37-7.26 (4H, m), 6.98 (1H, s), 6.48 (1H, brs), 6.41 (0.5H, brs), 4.09-4.04 (1H, m), 3.31-3.28 (1H, m), 3.21-3.18 (1H, m), 3.12-3.07 (1H, m), 2.86-2.83 (2H, m), 2.13 (3H, s), 2.06-2.03 (1H, m), 1.92-1.89 (1H, m), 1.61-1.48 (2H, m); ESI-MS m/z 489, 491 (MH+). |
| Example 16 | 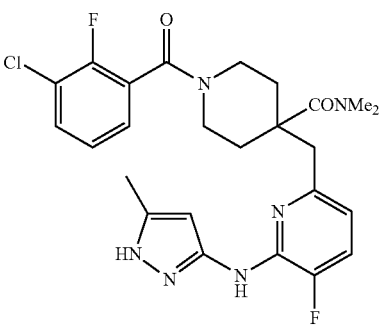 | $^1$H-NMR (DMSO-D$_6$) δ: 11.74 (1H, brs), 7.65 (1H, td, J = 7.7, 1.6 Hz), 7.37-7.26 (3H, m), 6.49-6.47 (1H, m), 6.17 (1H, brs), 4.13-4.10 (1H, m), 3.30-3.28 (1H, m), 3.15-2.86 (10H, m), 2.23-2.19 (1H, m), 2.15 (3H, s), 2.11-2.07 (1H, m), 1.66-1.50 (2H, m); ESI-MS m/z 517, 519 (MH+). |
| Example 17 | 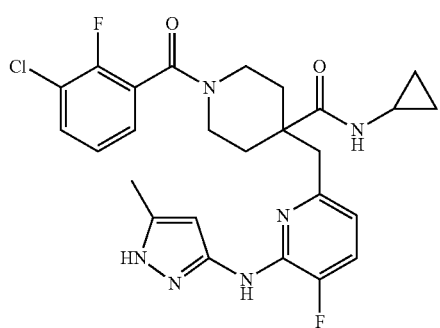 [SMILES: Cc1cc(Nc2nc(CC3(C(=O)NC4CC4)CCN(C(=O)c4cccc(Cl)c4F)CC3)ccc2F)n[nH]1] | $^1$H-NMR (DMSO-D$_6$) δ: 11.81 (1H, brs), 7.68-7.63 (2H, m), 7.38-7.26 (3H, m), 6.41 (1H, brs), 4.08-4.04 (1H, m), 3.29-3.27 (1H, m), 3.14-3.02 (2H, m), 2.84 (2H, brs), 2.51-2.46 (1H, m), 2.12 (3H, s), 2.09-2.05 (1H, m), 1.95-1.92 (1H, m), 1.60-1.47 (2H, m), 0.53-0.48 (2H, m), 0.34-0.31 (2H, m); ESI-MS m/z 529, 531 (MH+). |

TABLE 14

| Example | Structural formula | Physical property value |
|---|---|---|
| Example 18 | 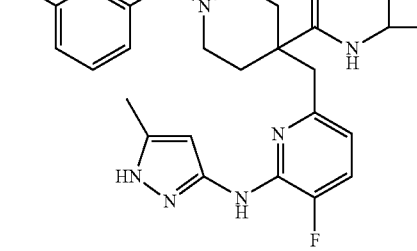 | ¹H-NMR (DMSO-D$_6$) δ: 11.80 (1H, brs), 8.67 (0.5H, brs), 7.71 (1H, d, J = 7.6 Hz), 7.66 (1H, td, J = 7.6, 1.5 Hz), 7.39-7.29 (2H, m), 7.28 (1H, t, J = 7.8 Hz), 6.38 (1.5H, brs), 4.17-4.15 (1H, brm), 4.06-4.03 (1H, brm), 3.31-3.29 (1H, m), 3.19-3.16 (1H, m), 3.07-3.02 (1H, m), 2.83 (2H, brs), 2.13 (3H, s), 1.94-1.93 (1H, m), 2.07-2.05 (1H, m), 2.00-1.96 (2H, m), 1.87-1.78 (2H, m), 1.63-1.49 (4H, m); ESI-MS m/z 543, 545 (MH+). |
| Example 19 | 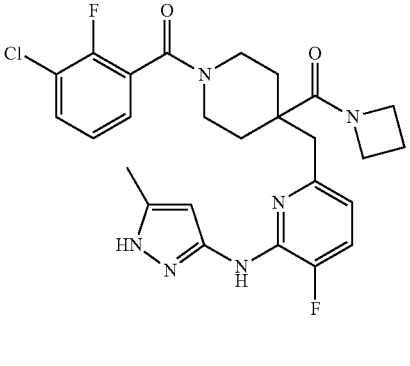 [SMILES: Cc1cc(Nc2nc(CC3(C(=O)N4CCC4)CCN(C(=O)c4cccc(Cl)c4F)CC3)ccc2F)n[nH]1] | ¹H-NMR (DMSO-D$_6$) δ: 8.99 (1H, brs), 7.66 (1H, td, J = 7.7, 1.5 Hz), 7.42-7.35 (2H, m), 7.29 (1H, t, J = 7.7 Hz), 6.54-6.51 (1H, m), 6.27 (1H, brs), 4.14-4.10 (1H, m), 3.87-3.72 (4H, m), 3.36-3.34 (1H, m), 3.13-3.00 (2H, m), 2.82 (2H, s), 2.15 (3H, s), 2.08-2.02 (1H, m), 1.95-1.88 (3H, m), 1.56-1.45 (2H, m); ESI-MS m/z 529, 531 (MH+). |
| Example 20 | 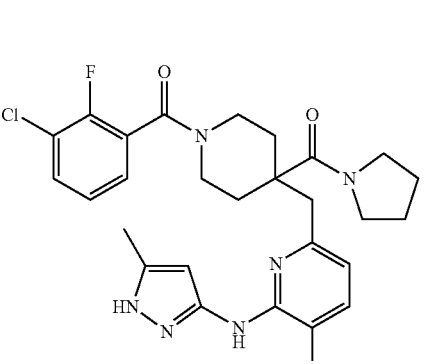 | ¹H-NMR (DMSO-D$_6$) δ: 11.80 (1H, brs), 8.69 (1H, brs), 7.65 (1H, td, J = 7.7, 1.7 Hz), 7.38-7.29 (2H, m), 7.29 (1H, t, J = 7.7 Hz), 6.57-6.36 (2H, m), 4.14-4.10 (1H, m), 3.34-3.27 (5H, m), 3.15-3.02 (2H, m), 2.87 (2H, brs), 2.26-2.22 (1H, m), 2.12-2.10 (1H, m), 2.15 (3H, s), 1.65-1.53 (6H, m); ESI-MS m/z 543, 545 (MH+). |

TABLE 15

| Example | Structural formula | Physical property value |
|---|---|---|
| Example 21 | 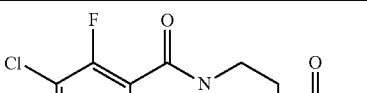 | ¹H-NMR (CDCl$_3$) δ: 7.42 (1H, ddd, J = 8.0, 7.1, 1.7 Hz), 7.23 (1H, brs), 7.17 (1H, dd, J = 10.5, 8.0 Hz), 7.12 (1H, dd, J = 8.0, 7.1 Hz), 7.07 (1H, brs), 6.53-6.50 (1H, m), 5.85 (1H, s), 4.48-4.45 (1H, m), 4.13-4.07 (2H, m), 3.84-3.73 (2H, m), 3.39-3.37 (2H, brm), 3.24-3.12 (2H, m), 3.03 (1H, d, J = 13.7 Hz), 2.52 (1H, d, J = 13.7 Hz), 2.37-2.29 (3H, m), 2.26 (3H, s), 1.67-1.42 (2H, m); ESI-MS m/z 545, 547 (MH+). |

TABLE 15-continued

| Example | Structural formula | Physical property value |
|---|---|---|
| Example 22 | 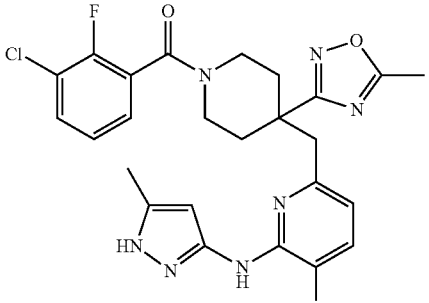 | $^1$H-NMR (CDCl$_3$) δ: 7.45 (1H, ddd, J = 8.2, 6.6, 1.3 Hz), 7.34-7.15 (1H, m), 7.15 (1H, t, J = 7.7 Hz), 7.14 (1H, dd, J = 10.6, 8.1 Hz), 7.03 (1H, brs), 6.42-6.31 (1H, m) 5.98 (1H, s), 4.63-4.52 (1H, m) 3.50-3.38 (1H, m), 3.17 (1H, brs), 3.10 (1H, d, J = 13.2 Hz), 3.05 (1H, d, J = 13.2 Hz), 3.02-2.89 (1H, m), 2.53-2.39 (1H, m), 2.51 (3H, s), 2.37-2.26 (1H, m), 2.31 (3H, s), 1.96-1.66 (2H, m); ESI-MS m/z 528, 530 (MH+). |
| Example 23 | 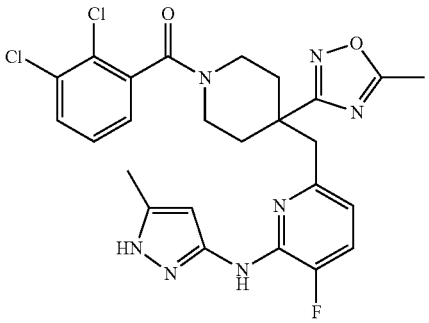 [SMILES: Cc1cc(Nc2nc(CC3(c4noc(C)n4)CCN(C(=O)c4cccc(Cl)c4Cl)CC3)ccc2F)n[nH]1] | $^1$H-NMR (CDCl$_3$) δ 7.50-7.47 (1H, m), 7.28-7.23 (1H, m), 7.16-7.08 (2H, m), 6.38-6.33 (1H, m), 6.04-5.99 (1H, m), 4.60 (1H, d, J = 13.9 Hz), 3.37-3.29 (1H, m), 3.19-3.03 (3H, m), 3.01-2.91 (1H, m), 2.52-2.43 (4H, m), 2.32-2.27 (4H, m) 1.98-1.84 (2H, m); ESI-MS m/z 544, 546 (MH+). |

TABLE 16

| Example | Structural formula | Physical property value |
|---|---|---|
| Example 24 | 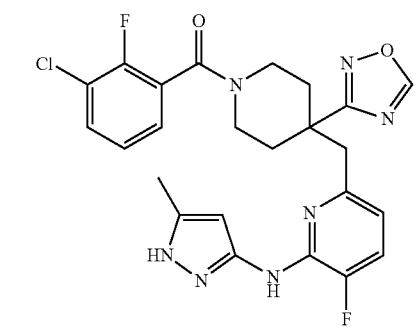 [SMILES: Cc1cc(Nc2nc(CC3(c4ncon4)CCN(C(=O)c4cccc(Cl)c4F)CC3)ccc2F)n[nH]1] | $^1$H-NMR (CDCl$_3$) δ: 8.73 (1H, s), 7.46 (1H, t, J = 7.5 Hz), 7.32-7.10 (3H, m), 7.00 (1H, s), 6.37 (1H, brs), 5.92 (1H, s), 4.63-4.52 (1H, m), 3.52-3.40 (1H, m), 3.27-2.88 (4H, m), 2.54-2.43 (1H, m), 2.40-2.30 (1H, m), 2.31 (3H, s), 2.02-1.68 (2H, m); ESI-MS m/z 514, 516 (MH+). |
| Example 25 | 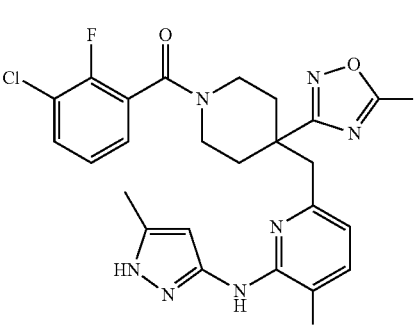 | $^1$H-NMR (CDCl$_3$) δ: 7.46 (1H, ddd, J = 8.3, 6.7, 1.2 Hz), 7.26-7.17 (2H, m), 7.16 (1H, t, J = 7.7 Hz), 7.12 (1H, dd, J = 10.6, 8.0 Hz), 6.28 (1H, dd, J = 7.0, 2.4 Hz), 6.15 (1H, brs), 4.64-4.50 (1H, m), 3.60-3.43 (1H, m), 3.24-2.92 (4H, m), 2.56-2.45 (1H, m), 2.42-2.34 (1H, m), 2.32 (3H, s), 2.09-1.81 (2H, m); ESI-MS m/z 582, 584 (MH+) |

TABLE 16-continued

| Example | Structural formula | Physical property value |
| --- | --- | --- |
| Example 26 | | $^1$H-NMR (CDCl$_3$) δ: 7.44 (1H, ddd, J = 8.3, 6.5, 1.0 Hz), 7.30-7.10 (3H, m), 6.86 (1H, d, J = 8.1 Hz), 6.39 (1H, brs), 5.72 (1H, s), 4.64-4.49 (1H, m), 3.86 (3H, s), 3.49-3.35 (1H, m), 3.28-2.85 (2H, m), 3.06 (2H, s), 2.52 (3H, s), 2.49-2.39 (1H, m), 2.37-2.28 (1H, m), 2.27 (3H, s), 1.94-1.64 (2H, m); ESI-MS m/z 540, 542 (MH+). |
| Example 27 | | $^1$H-NMR (CDCl$_3$) δ 7.50-7.39 (2H, m), 7.36-7.09 (2H, m), 6.42-6.30 (1H, m), 6.04-5.89 (1H, m), 4.61-4.50 (1H, m), 3.50-3.39 (1H, m), 3.29-2.88 (4H, m), 2.52-2.38 (4H, m), 2.36-2.20 (4H, m), 1.95-1.78 (2H, m); ESI-MS m/z 544, 546 (MH+). |

TABLE 17

| Example | Structural formula | Physical property value |
| --- | --- | --- |
| Example 28 | | $^1$H-NMR (CDCl$_3$) δ: 7.46 (1H, ddd, J = 8.3, 6.7, 1.3 Hz), 7.33-7.20 (2H, brm), 7.16 (1H, t, J = 7.5 Hz), 7.14 (1H, dd, J = 10.6, 7.9 Hz), 6.34 (1H, dd, J = 7.8, 2.1 Hz), 6.07 (1H, s), 4.66-4.57 (1H, m), 3.53-3.45 (1H, m), 3.20 (1H, brs), 3.09 (1H, d J = 13.4 Hz), 3.05 (1H, d, J = 13.4 Hz), 3.00-2.84 (1H, m), 2.52-2.43 (1H, m), 2.43-2.34 (1H, m), 2.38 (3H, s), 2.32 (3H, s), 2.01-1.66 (2H, m); ESI-MS m/z 528, 530 (MH+). |
| Example 29 | | $^1$H-NMR (CDCl$_3$) δ: 7.45 (1H, ddd, J = 8.3, 6.7, 1.3 Hz), 7.34-7.16 (2H, m), 7.14 (1H, t, J = 7.8 Hz), 7.11 (1H, dd, J = 10.7, 7.8 Hz), 6.34-6.20 (1H, m), 6.11 (1H, s), 4.66-4.50 (1H, m), 3.58-3.40 (1H, m), 3.20-3.02 (1H, m), 3.10 (2H, s), 3.01-2.88 (1H, m), 2.58-2.45 (1H, m), 2.43-2.30 (1H, m), 2.32 (3H, s), 2.26 (3H, s), 2.03-1.65 (2H, brm); ESI-MS m/z 523, 530 (MH+). |

TABLE 18

| Example | Structural formula | Physical property value |
|---|---|---|
| Comparative Example 1 | | 1H-NMR (CDCl$_3$) δ: 7.60 (1H, m), 7.55-7.20 (4H, m), 6.81 (1H, m), 6.58-6.20 (2H, m), 4.45 (1H, m), 3.48 (1H, m), 3.35-3.12 (2H, m), 3.04 (2H, s), 2.28 (1H, m), 2.15 (1H, m), 1.94-1.77 (2H, m); ESI-MS m/z 498, 500 (MH+). |
| Comparative Example 2 | | 1H-NMR (DMSO-D$_6$) δ 7.68-7.60 (1H, m), 7.58-7.43 (1H, m), 7.40-7.00 (3H, m), 6.72 (1H, s), 6.50 (1H, s), 4.32-4.20 (1H, m), 3.38-3.28 (1H, m), 3.09-2.88 (3H, m), 2.13-1.40 (5H, m), 1.13-1.00 (2H, m), 0.84-0.65 (2H, m); ESI-MS m/z 515, 517 (MH+). |
| Comparative Example 3 | | $^1$H-NMR (CDCl$_3$) δ: 7.50-7.10 (3H, m), 6.55-6.41 (1H, m), 6.25 (1H, s), 5.70-5.50 (1H, m), 4.45-4.20 (1H, m), 3.40-3.09 (5H, m), 2.32-1.95 (5H, m), 1.85-1.20 (3H, m), 1.15-1.00 (2H, m), 0.87-0.65 (2H, m); ESI-MS m/z 512, 514 (MH+). |
| Comparative Example 4 | | $^1$H-NMR (CDCl$_3$) δ: 7.48 (1H, t, J = 7.4 Hz), 7.24-7.16 (2H, m), 7.10 (1H, d, J = 8.8 Hz), 6.99 (1H, s), 6.41 (1H, s), 6.19 (1H, brs), 4.73-4.55 (1H, m), 3.83 (3H, s), 3.58-3.44 (1H, m), 3.39-2.96 (4H, m), 2.49-2.14 (2H, m), 1.89-1.44 (2H, m); ESI-MS m/z 505, 507 (MH+) |
| Comparative Example 5 | | $^1$H-NMR (CD3OD) δ: 7.90-7.85 (1H, m), 7.69 (1H, brs), 7.10-7.02 (1H, m), 6.95-6.87 (1H, m), 6.11 (1H, brs), 4.53-4.42 (1H, m), 3.55-3.45 (1H, m), 3.30-3.05 (4H, m), 2.33-2.26 (1H, m), 2.20-2.08 (1H, m), 1.80-1.58 (2H, m); ESI-MS m/z 458, 460 (MH+). |

TABLE 18-continued

| Example | Structural formula | Physical property value |
|---|---|---|
| Comparative Example 6 | 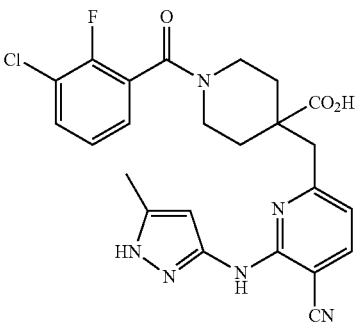 [SMILES: Cc1cc(Nc2nc(CC3(C(=O)O)CCN(C(=O)c4cccc(Cl)c4F)CC3)ccc2C#N)n[nH]1] | $^1$H-NMR (CDCl$_3$) δ: 9.03 (1H, d, J = 8.6 Hz), 7.49 (1H, t, J = 7.5 Hz), 7.31-7.24 (1H, m), 7.28 (1H, d, J = 8.6 Hz), 7.20 (1H, t, J = 7.5 Hz), 6.14 (1H, s), 4.56-4.37 (1H, m), 3.50-3.41 (1H, m), 3.23 (2H, s), 3.11-2.90 (2H, m), 2.53 (3H, s), 2.36-2.26 (2H, m), 2.22-2.13 (2H, m), 1.80-1.46 (2H, m); ESI-MS m/z 497, 499 (MH+). |
| Comparative Example 7 | 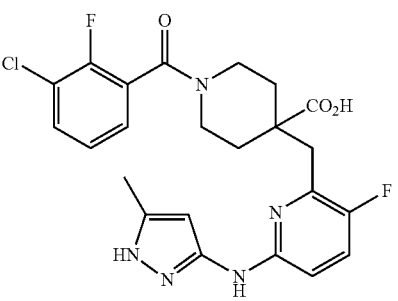 [SMILES: Cc1cc(Nc2ccc(F)c(CC3(C(=O)O)CCN(C(=O)c4cccc(Cl)c4F)CC3)n2)n[nH]1] | $^1$H-NMR (CDCl$_3$) δ: 7.55-7.42 (1H, m), 7.35-7.10 (3H, m), 6.57 (1H, dd, J = 9.2, 2.9 Hz), 5.52 (1H, s), 4.50-4.40 (1H, m), 3.45-3.04 (5H, m), 2.26-2.19 (1H, m), 2.23 (3H, s), 2.15-2.05 (1H, m), 1.71-1.40 (2H, m); ESI-MS m/z 490, 492 (MH+). |

Test Example 1: Evaluation of Inhibitory Activities on Aurora A and Aurora B

The inhibitory activity of a test compound on aurora A and aurora B was measured in accordance with the following method. As a control compound, MLN8237, which is under clinical development as an aurora A-selective inhibitor, was used.

1) Purification of Aurora A Protein

The cDNA encoding human aurora A having a N-term fused histidine tag was inserted into an expression vector and this protein was expressed at a high level in the *E. coli* BL21-CodonPlus (DE3)-RIL strain. The *E. coli* were collected and solubilized, and histidine tag-fused human aurora A protein was extracted by adsorption to a nickel chelate column and then eluted with imidazole from the column. The active fraction was desalted with a desalting column, whereby a purified enzyme was obtained.

2) Measurement of the Inhibitory Activity on Aurora A

For in vitro method for measuring the inhibitory activity of the aforementioned compounds on the aurora A kinase activity was carried out referring to the method described in JP-A-2008-81492. As the first step of measuring the inhibitory activity of the compound, the test compound was serially diluted with dimethyl sulfoxide (DMSO). Subsequently, purified human aurora A protein, FL-Peptide 21 (Caliper Life Sciences, Inc., a final concentration of 100 nM), ATP (a final concentration of 5 μM), and the solution of the compound of the present invention in DMSO (a final DMSO concentration of 5%) were added to a reaction buffer [50 mM Tris-hydrochloric acid buffer (pH 7.4), 15 mM magnesium acetate, and 0.2 mM ethylenediamine-N, N, N', N'-tetraacetic acid (EDTA)]. Then, the resulting mixture was incubated at 25° C. for 50 minutes to carry out kinase reactions. Then, the IMAP® Progressive Binding Reagent diluted 500-fold with the IMAP® Progressive Binding Buffer A (the product of Molecular Devices, LLC.) was added thereto to terminate the kinase reaction. After leaving the resulting product to stand in the dark at room temperature for 120 minutes, the amount of phosphorylation was determined from the degree of fluorescence polarization as measured by the PHERAstar (BMG LABTECH, excitation wavelength of 485 nm, detection wavelength of 520 nm). Then, the concentration of the compound at which the phosphorylation reaction can be inhibited by 50% was defined as the IC$_{50}$ value (nM), and the results were shown in Table 19.

3) Measurement of the Aurora B Kinase Activity

The in vitro method for measuring the inhibitory activity of the test compound on the aurora B kinase activity was performed in a similar manner as the above method for aurora A, and purified recombinant human aurora B protein was purchased from Carna Biosciences, Inc. The reaction buffer has the following composition: 20 mM HEPES (pH 7.4), 2 mM DTT, 0.01% Tween-20, magnesium chloride at a final concentration of 1 mM, and ATP at a final concentration of 40 μM, and the incubation time was 60 minutes. The concentration of the compound at which the phosphorylation reaction can be inhibited by 50% was defined as the IC$_{50}$ value (nM) and the results were shown in Table 19.

TABLE 19

| Example No. | Aurora A IC$_{50}$ (nM) | Aurora B IC$_{50}$ (nM) |
|---|---|---|
| 1 | 0.4 | 140 |
| 2 | 0.5 | 340 |
| 11 | 0.6 | 930 |
| 12 | 0.4 | 260 |
| 13 | 0.4 | 180 |
| 14 | 0.9 | 460 |
| 17 | 0.9 | 900 |
| 19 | 1.0 | 680 |
| 22 | 0.7 | 380 |
| 24 | 0.5 | 190 |

TABLE 19-continued

| Example No. | Aurora A IC$_{50}$ (nM) | Aurora B IC$_{50}$ (nM) |
|---|---|---|
| 28 | 0.7 | 450 |
| 29 | 0.8 | 390 |
| Comparative Example 6 | 220 | 320 |
| MLN8237 | 0.6 | 90 |

As a result, it was confirmed that the compounds of the present invention exhibited a higher inhibitory activity on aurora A and a lower inhibitory activity on aurora B even in comparison with MLN8237, which is the control compound, thereby exhibiting selectivity for aurora A. In contrast, Comparative Example 6 did not exhibit either inhibitory activity on aurora A or selectivity for aurora A. From the above results, it was suggested that incorporation of a specific substituent into the specific position (a halogen atom or a $C_1$-$C_6$ alkoxy group at $R_2$) on the pyridine ring in the structure of the compound of the present invention represented by the general formula (I) could impart not only a high inhibitory activity on aurora A, but also aurora A selectivity.

Test Example 2: Evaluation of the Inhibitory Effect on Cell Proliferation

Cells of the human-derived stomach cancer cell line SNU-16 were each routinely subcultured in the 10% fetal bovine serum (FBS)-containing RPMI-1640 medium and 10% FBS-containing Dulbecco's Modified Eagle Medium (DMEM) in order to maintain cell density of no more than 80%. In order to initiate a test for the inhibitory activity on cell proliferation, cells were each suspended in the aforementioned medium and seeded in each well of a 96-well flat bottom plate (black plate with a transparent bottom) at 2,500 or 3,000 cells per well. The cells were then cultured for one day at 37° C. in an incubator containing 5% carbon dioxide gas. The next day, the compound of the present invention and the subject compound were dissolved in DMSO, and using DMSO, the test compounds were serially diluted to a concentration of 200 times the final concentration. The solution of the test compounds in DMSO was diluted with the medium used for culturing, and then added to each well of the cell culture plate at a final DMSO concentration of 0.5%. The cells were cultured for 72 hours at 37° C. in an incubator containing 5% carbon dioxide gas. The cells were counted at the time of addition of the test compounds and 72 hours after culturing using the CellTiter-Glo Luminescent Cell Viability Assay kit (the product of Promega) based on the protocol recommended by Promega. The reagent included in the kit was added to each plate, followed by stirring, and the plates were left to stand at room temperature for 10 minutes. Upon completion of the reaction, the luminescence signal was measured using a microplate reader.

The cell proliferation inhibitory rate was calculated from the following formula and the concentration of the test compound at which the cell proliferation was inhibited by 50% (GI$_{50}$ (nM)) was determined. The results were shown in Table 20.

Cell proliferation inhibitory rate (%)=$(C-T)/(C-C0) \times 100$

T: Luminescence signal in a well with the addition of the test compound
C: Luminescence signal in a well without the addition of the test compound
C0: Luminescence signal in a well measured before the addition of the compound

TABLE 20

| Example No. | GI$_{50}$ (nM) |
|---|---|
| 1 | 120 |
| 13 | 60 |
| 22 | 970 |

As a result, the compound of the present invention exhibited the inhibitory effect on cell proliferation, and thus was suggested to be useful as an anti-tumor agent.

Test Example 3: Evaluation of Oral Absorbability

The test compound was suspended or dissolved in 0.5% HPMC and orally administered to a BALB/cA mouse. The blood was drawn from the retro-orbital venous plexus 0.5, 1, 2, 4, and 6 hours after oral administration to obtain plasma. The concentration of the compound in the plasma thus obtained was measured by LCMS and the oral absorbability was evaluated.

As a result, after oral administration, adequate plasma concentrations were observed with the compounds of Examples 1, 11, 12, 13, and 22, which are the compounds of the present invention, showing favorable oral absorbability. Meanwhile, Comparative Examples 2 to 5 and 7 did not exhibit adequate oral absorbability (AUC$_{0-6hr}$ was less than ⅛ of that of the compounds of the present invention). Therefore, it was considered difficult to incorporate those compounds in orally administered preparations as the active ingredient, and thus no clinical effect would be expected from oral administration. From the above results, it was revealed that incorporation of a halogen atom or a $C_1$-$C_6$ alkoxy group at $R_2$ on the pyridine ring in the structure of the compound of the present invention represented by the general formula (I) imparted high oral absorbability.

Test Example 4: Evaluation of the Anti-Tumor Effect (1)

The luciferase-introduced human uterine cervical cancer cell line (Hela-Luc) was subcutaneously transplanted into a nude mouse, and when the volume of the grafted tumor reached 100 to 200 mm³, five mice in one group were grouped into the single drug administration group and combinational administration group by a randomized stratification method so as to achieve a uniform tumor volume in each group (day 1). In the single drug administration groups, Group 1: paclitaxel (30 mg/kg) was intravenously administered on day 1, Group 2: the compound of the present invention (Compound 1) (60 mg/kg) was orally administered twice a day on day 2 and day 3, and Group 3: Comparative Compound 1 (60 mg/kg) was orally administered twice a day on day 2 and day 3. In the combination administration groups, Group 4: paclitaxel (30 mg/kg) was intravenously administered on day 1 and Compound 1 (60 mg/kg) was orally administered twice a day on day 2 and day 3, and Group 5: paclitaxel (30 mg/kg) was intravenously administered on day 1 and Comparative Compound 1 (60 mg/kg) was orally administered twice a day on day 2 and day 3. In order to compare the anti-tumor effect brought about by drug administration, setting the tumor volume at the time of grouping at 1, the relative tumor volume (RTV) was determined in accordance with the following formula as a rate of tumor proliferation.

RTV=(Tumor volume on the day of measurement of tumor volume)/(Tumor volume at the time of grouping)

In Table 21, the average RTV values of the control and single drug administration groups (Groups 2 and 3) on the 23$^{rd}$ day after grouping are shown, and the average RTV values of the paclitaxel-only administered group (Group 1) and the combination administration groups (Groups 4 and 5) on the 23$^{rd}$ and 46$^{th}$ days after grouping are shown.

Also, the disease control rate (DCR) described in, for example, J. Clin. Oncol., 29 (31), pp. 4129 to 4136, (2010) was also used as the index of the anti-tumor effect brought about by drug administration. DCR was defined as the ratio of individuals in which RTV does not exceed 1 on the final day of tumor volume measurement (day 46). DCR was obtained in accordance with the following formula and the results were shown in Table 21.

DRC (%)=[(Number of individuals in which RTV does not exceed 1 on the final day of tumor volume measurement)/(Number of mice survived on the final day)]×100

Meanwhile, as the index of systemic toxicity caused by drug administration, the body weight change (BWC) was used. BWC was calculated in accordance with the following formula and the average BWC values were shown in Table 21.

BWC (%)=([(Body weight of mouse on the day of body weight measurement)−(Body weight of mouse at the time of grouping)]/(Body weight of mouse at the time of grouping))×100

TABLE 21

| Group | Day 23 | | Day 46 | | |
|---|---|---|---|---|---|
| | RTV | BWC | RTV | BWC | DCR |
| Control | 15.66 | 11.3 | | | |
| 1. Paclitaxel | 0.69 | 3.0 | 5.38 | 11.6 | 40% |
| 2. Compound 1 | 10.47 | 11.6 | | | |
| 3. Comparative Compound 1 | 15.23 | 11.6 | | | |
| 4. Compound 1/Paclitaxel | 0.08 | 2.2 | 0.61 | 9.4 | 80% |
| 5. Comparative Compound 1/Paclitaxel[#] | 0.29 | −3.9 | 3.95 | 6.7 | 25% |

[#]One mouse died out of five mice on day 29

As a result, in comparison with the paclitaxel-only administered group (Group 1), the anti-tumor effect was remarkably potentiated in the group given combination administration of the compound of the present invention (Compound 1) and paclitaxel (Group 4) without greatly increasing toxicity, which is manifested as, for example, a decrease in body weight. Also, from the RTV and DCR values on day 46 of administration, it was found that a continuous tumor reducing effect could be expected from the administration of Compound 1. Meanwhile, as apparent from the RTV and DCR values on day 23 and day 46 of administration, Comparative Compound 1 did not clearly potentiate the anti-tumor effect when administered in combination with paclitaxel (Group 5), in comparison with the paclitaxel-only administered group (Group 1).

Test Example 5: Evaluation of the Anti-Tumor Effect (2)

By a similar method to that used in Test Example 4, the luciferase-introduced human uterine cervical cancer cell line (Hela-Luc) was subcutaneously transplanted into a nude mouse, and five mice in one group were grouped into the single drug administration group and combination administration group by a randomized stratification method (day 1). In the single drug administration groups, paclitaxel (20 mg/kg) was intravenously administered on day 1. Also, Compound 13 (30 mg/kg) or Compound 22 (100 mg/kg) was orally administered twice a day on day 2 and day 3. In the combination administration groups, paclitaxel (20 mg/kg) was intravenously administered on day 1, and Compound 13 (30 mg/kg) or Compound 22 (60 mg/kg) was orally administered twice a day on day 2 and day 3. The average RTV and BWC values on the 11th day after grouping were shown in Tables 22 and 23.

TABLE 22

| | Day 11 | |
|---|---|---|
| Group | RTV | BWC |
| Control | 7.24 | 7.2 |
| Paclitaxel | 2.90 | 5.4 |
| Compound 13 | 6.54 | 6.0 |
| Compound 13/Paclitaxel | 0.72 | 4.2 |

TABLE 23

| | Day 11 | |
|---|---|---|
| Group | RTV | BWC |
| Control | 5.68 | 10.9 |
| Paclitaxel | 3.05 | 7.8 |
| Compound 22 | 4.66 | 6.9 |
| Compound 22/Paclitaxel | 1.73 | 2.8 |

As a result, in comparison with the paclitaxel-only administered group, the anti-tumor effect was remarkably potentiated in the group given combination administration of Compound 13 or Compound 22, both of which are the compounds of the present invention, and paclitaxel, without greatly increasing toxicity, which is manifested as, for example, a decrease in body weight.

Test Example 6: Measurement of the Aurora C Kinase Activity

The inhibitory activity of the compound of the present invention on the aurora C kinase activity was measured in vitro. Specifically, using the Off-chip Mobility Shift Assay, reactions were carried out by the following procedure.

To reaction buffer (20 mM HEPES, 0.01% Triton X-100, 2 mM DTT, pH 7.5), the compound of the present invention, ATP (a final concentration of 25 μM), substrates (Kemptide, a final concentration of 1000 nM), magnesium (a final concentration of 5 mM), and purified human aurora C kinase were added, followed by mixing. The reactions were then allowed to proceed at room temperature for one hour. To obtain purified human aurora C kinase, the GST protein was fused to the N-terminus of the full-length aurora C kinase, and the resulting protein was expressed by baculovirus. The GST-aurora C fused protein was purified by glutathione sepharose chromatography. Upon completion of the reaction, the reaction terminating solution (QuickScout Screening Assist MSA; Carna Biosciences, Inc.) was added, and the substrate peptide and phosphorylated peptide in the reaction solution were separated and quantitated by the LabChip 3000 system (Carna Biosciences, Inc.). The in vitro method for measuring the inhibitory activity of the compound of the present invention on the aurora C kinase activity was performed in accordance with the method for measuring the inhibitory activity on aurora A demonstrated in Test Example 1-2) above, and defining the concentration of the compound at which the phosphorylation reaction can be inhibited by 50% as the $IC_{50}$ value (nM), the resulting inhibitory activity on aurora C kinase was compared with the inhibitory activity on aurora A obtained in the aforementioned Test Example 1-2).

As a result, the inhibitory activity of the compound of the present invention on aurora C was 80 to 100 times as weak as the inhibitory activity on aurora A, suggesting a significant aurora A-selective inhibitory activity of the compound of the present invention.

Test Example 7: Action of Potentiating the Effect of Microtubule-Targeting Agents (In Vitro)

Cells of the human-derived stomach cancer cell line OCUM-2M and the human-derived uterine cancer cell line HeLa were routinely subcultured in the 10% fetal bovine serum (FBS)-containing Dulbecco's Modified Eagle Medium (DMEM) at a cell density of no more than 80%. In order to initiate a test for the inhibitory activity on cell proliferation, cells were each suspended in the aforementioned medium and seeded in each well of a 96-well flat bottom plate (black plate with a transparent bottom) at 2,500 or 3,000 cells per well. The cells were then cultured for one day at 37° C. in an incubator containing 5% carbon dioxide gas. The next day, serially diluted solutions of microtubule-targeting agents (docetaxel, cabazitaxel, and epothilone B) were prepared with DMSO (10 doses were prepared for each drug at a test concentration ranging from 0.03 nM to 1000 nM), and the solutions were diluted with the medium. Subsequently, the resulting solutions were added to each well of the cell culture plate at a final DMSO concentration of 0.1%. Also, in order to verify the combined effect of the microtubule-targeting agent and the compound of the present invention, the aforementioned compound was diluted with DMSO at a final concentration of 300 nM (a final DMSO concentration of 0.1%), and then added to each well of the cell culture plate. As the comparative control group, wells each containing the microtubule-targeting agent alone or the present compound alone were separately prepared and cultured in an incubator containing 5% carbon dioxide gas at 37° C. for 72 hours. The cells were counted using the CellTiter-Glo Luminescent Cell Viability Assay kit (the product of Promega) based on the protocol recommended by Promega. The reagent included in the kit was added to each plate, followed by stirring, and the plates were left to stand at room temperature for 10 minutes. Upon completion of the reaction, the luminescence signal was measured using a microplate reader.

The cell proliferation rate was calculated from the following formula, and the concentration of the test compound at which the cell proliferation was inhibited by 50% ($IC_{50}$ (μM)) was determined.

Cell proliferation rate (%)=$T/C$×100

T: Luminescence signal in a well with the addition of the test compound
C: Luminescence signal in a well without the addition of the test compound Further, the $IC_{50}$ value of the microtubule-targeting agent alone ($IC_{50\_}$ microtubule-targeting agent) and the $IC_{50}$ value of the microtubule-targeting agent in the combination administration of the microtubule agonist and the compound of the present invention ($IC_{50\_}$ combination administration) were determined. The latter $IC_{50}$ value ($IC_{50}$ value_combination administration) was calculated from the cell proliferation-inhibitory rate (converted value) in the combination administration group by defining the cell proliferation rate of the compound of the present invention alone as 100%. The degree of potentiation of the effect of the microtubule-targeting agent by the addition of the compound of the present invention was evaluated by the degree of the value calculated from the following formula.

(Potentiating effect of the combination administration)=($IC_{50}$ value_combination administration)/ ($IC_{50}$ value_ microtubule-targeting agent)

The evaluation was performed according to criteria by which the value of more than 1 was evaluated as exhibiting strong potentiating effect, while the value of less than or equal to 1 was evaluated as exhibiting poor potentiating effect.

As a result, by adding the compound of the present invention to microtubule-targeting agents such as docetaxel, cabazitaxel, and epothilone B, a value of larger than 2 was obtained from the above formula, indicating that the compound of the present invention potentiated the inhibitory effect of these microtubule agonists on cell proliferation.

As shown above, the compound of the present invention selectively and excellently inhibited aurora A, showing an excellent anti-tumor effect with favorable oral absorption. Also, the compound of the present invention was shown to strongly potentiate the anti-tumor effect of paclitaxel by in vivo tests using nude mice. Furthermore, the compound of the present invention was shown to potentiate also the inhibitory effect of microtubule-targeting agents other than paclitaxel on cell proliferation.

The invention claimed is:

1. A method for treating cancer, comprising:
   administering an effective dose of a piperidine compound of formula (I) or a salt thereof:

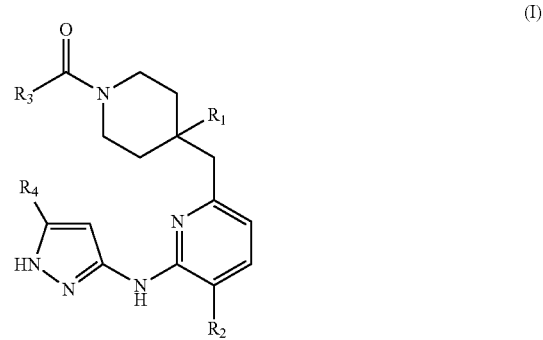

(I)

wherein $R_1$ is a carboxyl group, —C(=O)$NR_5R_6$, or an oxadiazolyl group optionally having a $C_1$-$C_6$ alkyl group or a trifluoromethyl group as a substituent;

$R_2$ is a halogen atom or a $C_1$-$C_6$ alkoxy group;

$R_3$ is a phenyl group optionally having 1 to 3 same or different group(s) selected from the group consisting of a halogen atom, a $C_1$-$C_6$ alkyl group, a $C_1$-$C_6$ alkoxy group, and a trifluoromethyl group as a substituent;

$R_4$ is a hydrogen atom or a $C_1$-$C_6$ alkyl group;

$R_5$ and $R_6$ are the same or different and are each independently a hydrogen atom, a $C_1$-$C_6$ alkyl group, or a $C_3$-$C_6$ cycloalkyl group, or $R_5$ and $R_6$ optionally form a 3 to 6-membered nitrogen-containing saturated heterocyclic group together with a nitrogen atom to which $R_5$ and $R_6$ are bound.

2. The method according to claim 1, wherein the cancer is selected from the group consisting of head and neck cancer, esophageal cancer, stomach cancer, duodenal cancer, colon cancer, rectal cancer, liver cancer, gallbladder and bile duct cancer, biliary tract cancer, pancreatic cancer, lung cancer, breast cancer, ovary cancer, uterine cervical cancer, uterine cancer, renal cancer, bladder cancer, prostate cancer, testicular cancer, bone and soft tissue sarcoma, hematologic cancer, multiple myeloma, skin cancer, brain tumor, mesothelioma, and hematologic cancer.

3. The method according to claim 1, wherein the cancer is selected from the group consisting of hematologic cancer, uterine cervical cancer, stomach cancer, breast cancer, prostate cancer, ovary cancer, lung cancer, and colon cancer.

4. A method for potentiating an anti-tumor effect of a microtubule-targeting agent, comprising:
administering an effective dose of a piperidine compound of formula (I) or a salt thereof:

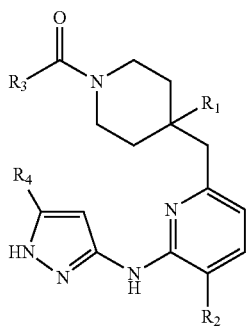

(I)

wherein $R_1$ is a carboxyl group, —C(=O)NR$_5$R$_6$, or an oxadiazolyl group optionally having a $C_1$-$C_6$ alkyl group or a trifluoromethyl group as a substituent;
$R_2$ is a halogen atom or a $C_1$-$C_6$ alkoxy group;
$R_3$ is a phenyl group optionally having 1 to 3 same or different group(s) selected from the group consisting of a halogen atom, a $C_1$-$C_6$ alkyl group, a $C_1$-$C_6$ alkoxy group, and a trifluoromethyl group as a substituent;
$R_4$ is a hydrogen atom or a $C_1$-$C_6$ alkyl group;
$R_5$ and $R_6$ are the same or different and are each independently a hydrogen atom, a $C_1$-$C_6$ alkyl group, or a $C_3$-$C_6$ cycloalkyl group, or $R_5$ and $R_6$ optionally form a 3 to 6-membered nitrogen-containing saturated heterocyclic group together with a nitrogen atom to which $R_5$ and $R_6$ are bound.

5. The method according to claim 4, wherein the anti-tumor effect is potentiated on cancer which is one of head and neck cancer, esophageal cancer, stomach cancer, duodenal cancer, colon cancer, rectal cancer, liver cancer, gallbladder and bile duct cancer, biliary tract cancer, pancreatic cancer, lung cancer, breast cancer, ovary cancer, uterine cervical cancer, uterine cancer, renal cancer, bladder cancer, prostate cancer, testicular cancer, bone and soft tissue sarcoma, hematologic cancer, multiple myeloma, skin cancer, brain tumor, mesothelioma, and hematologic cancer.

6. The method according to claim 4, wherein the anti-tumor effect is potentiated on cancer which is one of hematologic cancer, uterine cervical cancer, stomach cancer, breast cancer, prostate cancer, ovary cancer, lung cancer, and colon cancer.

7. The method according to claim 4, wherein the microtubule-targeting agent is a taxane anticancer agent.

8. The method according to claim 7, wherein the taxane anticancer agent comprises at least one selected from the group consisting of paclitaxel, docetaxel, and cabazitaxel.

9. The method according to claim 4, wherein the administering is performed such that a molar ratio of the microtubule-targeting agent and the compound of the formula (I) or a salt thereof is from 0.01 to 100.

10. The method according to claim 4, wherein the administering is performed such that a molar ratio of the microtubule-targeting agent and the compound of the formula (I) or a salt thereof is from 0.05 to 50.

11. The method according to claim 4, wherein the administering is performed such that a molar ratio of the microtubule-targeting agent and the compound of the formula (I) or a salt thereof is from 0.1 to 20.

12. A method for treating cancer, comprising:
administering an effective dose of a piperidine compound of formula (I) or a salt thereof and an effective dose of a microtubule-targeting agent:

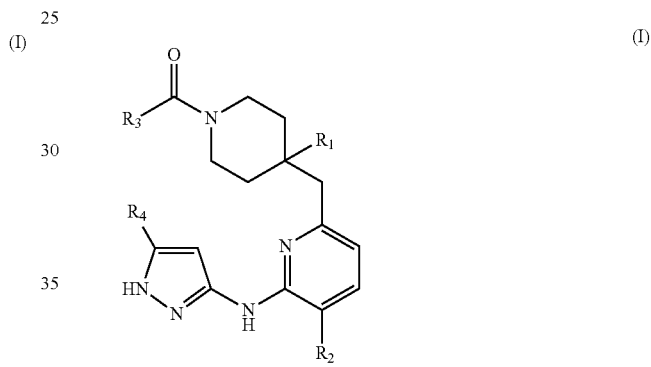

(I)

wherein $R_1$ is a carboxyl group, —C(=O)NR$_5$R$_6$, or an oxadiazolyl group optionally having a $C_1$-$C_6$ alkyl group or a trifluoromethyl group as a substituent;
$R_2$ is a halogen atom or a $C_1$-$C_6$ alkoxy group;
$R_3$ is a phenyl group optionally having 1 to 3 same or different group(s) selected from the group consisting of a halogen atom, a $C_1$-$C_6$ alkyl group, a $C_1$-$C_6$ alkoxy group, and a trifluoromethyl group as a substituent;
$R_4$ is a hydrogen atom or a $C_1$-$C_6$ alkyl group;
$R_5$ and $R_6$ are the same or different and are each independently a hydrogen atom, a $C_1$-$C_6$ alkyl group, or a $C_3$-$C_6$ cycloalkyl group, or $R_5$ and $R_6$ optionally form a 3 to 6-membered nitrogen-containing saturated heterocyclic group together with a nitrogen atom to which $R_5$ and $R_6$ are bound.

13. The method according to claim 12, wherein the cancer is one of head and neck cancer, esophageal cancer, stomach cancer, duodenal cancer, colon cancer, rectal cancer, liver cancer, gallbladder and bile duct cancer, biliary tract cancer, pancreatic cancer, lung cancer, breast cancer, ovary cancer, uterine cervical cancer, uterine cancer, renal cancer, bladder cancer, prostate cancer, testicular cancer, bone and soft tissue sarcoma, hematologic cancer, multiple myeloma, skin cancer, brain tumor, mesothelioma, and hematologic cancer.

14. The method according to claim 12, wherein the cancer is one of hematologic cancer, uterine cervical cancer, stomach cancer, breast cancer, prostate cancer, ovary cancer, lung cancer, and colon cancer.

15. The method according to claim 12, wherein the microtubule-targeting agent is a taxane anticancer agent.

16. The method according to claim 15, wherein the taxane anticancer agent comprises at least one selected from the group consisting of paclitaxel, docetaxel, and cabazitaxel.

17. The method according to claim 12, wherein the administering is performed such that a molar ratio of the microtubule-targeting agent and the compound of the formula (I) or a salt thereof is from 0.01 to 100.

18. The method according to claim 12, wherein the administering is performed such that a molar ratio of the microtubule-targeting agent and the compound of the formula (I) or a salt thereof is from 0.05 to 50.

19. The method according to claim 12, wherein the administering is performed such that a molar ratio of the microtubule-targeting agent and the compound of the formula (I) or a salt thereof is from 0.1 to 20.

20. The method according to claim 1, wherein the cancer is stomach cancer.

21. The method according to claim 1, wherein the piperidine compound of the formula (I) is 1-(2,3-dichlorobenzoyl)-4-((5-fluoro-6-(5-methyl-1H-pyrazol-3-ylamino)pyridin-2-yl)methyl)piperidine-4-carboxylic acid.

\* \* \* \* \*